(12) United States Patent
Nosrati

(10) Patent No.: US 9,950,103 B2
(45) Date of Patent: Apr. 24, 2018

(54) COMBINATION KIDNEY AND LIVER DIALYSIS SYSTEM AND METHOD

(71) Applicant: Micromedics Inc., Tarzana, CA (US)

(72) Inventor: Saeid Mordechai Nosrati, Tarzana, CA (US)

(*) Notice: Subject to any disclaimer, the term of this patent is extended or adjusted under 35 U.S.C. 154(b) by 275 days.

(21) Appl. No.: 15/060,405

(22) Filed: Mar. 3, 2016

(65) Prior Publication Data

US 2017/0252497 A1    Sep. 7, 2017

(51) Int. Cl.
| | |
|---|---|
| *A61M 1/16* | (2006.01) |
| *A61M 1/34* | (2006.01) |
| *A61K 38/38* | (2006.01) |
| *A61K 33/44* | (2006.01) |
| *A61K 31/795* | (2006.01) |

(52) U.S. Cl.
CPC ......... *A61M 1/1633* (2014.02); *A61K 31/795* (2013.01); *A61K 33/44* (2013.01); *A61K 38/38* (2013.01); *A61M 1/1654* (2013.01); *A61M 1/1676* (2014.02); *A61M 1/3413* (2013.01); *A61M 1/3417* (2014.02); *A61M 1/3431* (2014.02); *A61M 1/3479* (2014.02); *A61M 1/3482* (2014.02); *A61M 1/3496* (2013.01); *A61M 1/1698* (2013.01); *A61M 2202/07* (2013.01); *A61M 2202/08* (2013.01)

(58) Field of Classification Search
CPC ............ A61M 1/1633; A61M 1/1676; A61M 1/3417; A61M 1/3431; A61M 1/3479; A61M 1/3482; A61M 1/1654; A61M 1/3413; A61M 1/3496

USPC .............................................. 604/4.01–6.16
See application file for complete search history.

(56) References Cited

U.S. PATENT DOCUMENTS

| | | | | |
|---|---|---|---|---|
| 2005/0115898 | A1* | 6/2005 | Sternby | A61M 1/16 210/636 |
| 2009/0124963 | A1* | 5/2009 | Hogard | A61M 1/16 604/30 |
| 2012/0305486 | A1* | 12/2012 | Storr | A61M 1/16 210/646 |
| 2015/0273127 | A1* | 10/2015 | Flieg | A61M 1/3679 210/266 |

(Continued)

*Primary Examiner* — Philip R Wiest
(74) *Attorney, Agent, or Firm* — Elizabeth Yang

(57) ABSTRACT

A combination kidney and liver dialysis system and method provides a portable, lightweight hemodialysis device that removes uremic toxins, hepatic toxins, water, and impurities from the blood. The method comprises separating the blood into a plasma portion and a cellular portion, immediately returning the cellular portion to the body, providing large volumes of replacement fluids, diluting the plasma portion with replacement fluids, and then manipulating the plasma portion of the blood to pass through hemoperfusion membranes, hemodiafiltration membranes, and extracorporeal membrane oxygenation membranes. Dialysis is performed on the plasma portion of the blood with an albumin dialyzer against an albumin dialysate and a high molecular weight cut off membrane. Dialysis is performed on the plasma portion of blood with a lipid dialysate comprising 10-30% lipid composition, and a high flux dialyzer. The system can also use any form of dialysis technology including hollow fiber, flat plate and microfluidic technology.

25 Claims, 19 Drawing Sheets

(56) References Cited

U.S. PATENT DOCUMENTS

| | | | |
|---|---|---|---|
| 2015/0290380 A1* | 10/2015 | Welzel | B01D 63/02 210/638 |
| 2016/0022897 A1* | 1/2016 | Weigel | A61M 1/1694 210/638 |
| 2017/0021310 A1* | 1/2017 | Berzinis | B01D 67/0016 |
| 2017/0095603 A1* | 4/2017 | Cho | A61M 1/1623 |
| 2017/0282131 A1* | 10/2017 | Berzinis | A61M 1/1698 |

* cited by examiner

COMBINATION KIDNEY AND LIVER DIALYSIS SYSTEM AND METHOD

FIELD OF THE INVENTION

The present invention relates generally to a combination kidney and liver dialysis system and method for treating multiple organ dysfunction syndrome through multiple semi-permeable membranes and manipulations of the blood and its components More so, the combination kidney and liver dialysis system and method helps remove uremic toxins and hepatic toxins from the blood through a unique process involving diluting the blood, separating the blood into plasma and cellular portions, returning the cellular portion to the body, providing large volumes of replacement fluids, and passing the plasma portion through multiple strategically placed semi-permeable membranes and absorptive surfaces, including: diffusive, convective as well as adsorptive in CRRT, hemodialysis, hemodiafiltration, hemoperfusion, and the special albumin dialysis, and the unique lipid dialysis.

BACKGROUND OF THE INVENTION

It is known that dialysis is a life-support treatment that uses a special machine to filter harmful wastes, salt, and excess fluid from your blood. This restores the blood to a normal, healthy balance. However the current dialysis can barely replace 10% of renal function. Currently in use Hollow Fiber based Dialysis replaces only limited number of kidney's important functions.

As for liver replacement there is no liver dialysis available. Generally, dialysis works on the principles of the diffusion of solutes and ultrafiltration of fluid across a semi-permeable membrane. Blood flows by one side of a semi-permeable membrane, and a dialysate, or special dialysis fluid, flows by the opposite side. Smaller solutes and fluid pass through the membrane, but the membrane blocks the passage of larger substances, such as red blood cells, large proteins. This replicates the filtering process that takes place in the kidneys, when the blood enters the kidneys and the larger substances are separated from the smaller ones in the glomerulus.

It is known that treatment options for liver disease are limited. Liver transplantation is the favored treatment for serious liver disease or liver failure. However, the number of suitable liver donors varies and is not always sufficient to meet the demand for liver transplant operations. Generally, liver dialysis is a detoxification treatment for liver failure and is currently not available for patients with various liver disorders, such as, for example, hepatorenal syndrome, decompensated chronic liver disease, acute liver failure, graft dysfunction after liver transplantation, liver failure after liver surgery, secondary liver failure and multi organ failure. It is recognized that a critical issue of the clinical syndrome in liver failure is the accumulation of toxins not cleared by the failing liver. Thus, there is a great unmet need for a way to treat patients with liver failure just like kidney failure patients.

Typically, the function of the normal, healthy kidney in the animal body is to act as a filter for the blood circulating through the body, to remove impurities therefrom and restore correct blood composition balance. When the kidneys cease to function, artificial kidneys can be employed in their place, such an artificial kidney comprising a flexible dialysis membrane used outside the body as a separate treatment apparatus for blood dialysis or filtration purposes.

One common method for treating failed kidneys involves standard dialysis, in which blood from the body is circulated past one side of the membrane and special dialysis fluid is circulated past the other side of the membrane, so as to adjust and correct the blood composition by osmosis, diffusion, convection, adsorption and ultrafiltration across the membrane. The hepatic toxins are difficult to be removed via dialysis. Also, there is no liver dialysis because liver toxins are protein-bound and are not dialyzeable.

In many instances, patients with one or more failing organs or organ systems would not be able to survive without medical assistance and supportive care. The organs that often fail require life support, however not all organ systems have a replacement or supportive device. The most common types of life support are for the respiratory, cardiovascular, and renal systems. Currently, support systems or replacement systems are non-existent for the liver.

In addition, currently in spite of renal replacement therapies, the favorable outcome of patients with acute kidney failure is less than 50 percent. The mortality even is higher when other organs fail concurrently or sequentially. Multi-Organ Dysfunction Syndrome (MODS) evolves in the wake of a profound disruption of systemic homeostasis. The intriguing concept, hence, of applying more extracorporeal devices for the therapy and support of several organs during (MODS) is appealing and opens the hypothesis of a complex integrated platform that might be defined "multiple organ support therapy" (MOST). At present there is no agent that can reverse the established organ failure.

Therapy therefore is limited to supportive care, i.e. safeguarding hemodynamic, and respiration. Maintaining adequate tissue oxygenation is a principal target. Organ replacement therapy is available for renal failure even though it is not that effective. Even worse, there is no therapy for liver failure except liver transplantation. Mortality of MODS varies from 30% to 100% where the chance of survival is diminished as the number of organs involved increases. Since the 1980s the mortality rate has not changed.

Those skilled in the art, in light of the present teachings, will recognize that microdialysis is a widely employed technique for sampling the chemistry of the extracellular space in vivo. It is unique in its ability to dynamically sample the extracellular fraction of a range of molecules of interest. It has been used in both human and animal studies in the brain and other organs. The technique is now routinely established in several neurointensive care units for bedside monitoring of small molecules related to energy metabolism.

Over recent years, with the advent of membranes with relatively higher molecular weight cut-off (MWCO) dialysis has been drawing wider application with an increasing range of molecules being assayed in the laboratory, including those of higher molecular weights such as cytokines. The relative recovery (RR, also termed extraction efficiency) is defined as the percentage concentration of a molecule in the interstitial fluid (in vivo) or external solution (in vitro) that is collected in the microdialysate.

Other proposals have involved dialysis systems for the liver and kidneys. The problem with these devices is that they do not provide sufficient removal of toxins and water. Thus, an unaddressed need exists in the industry to address the aforementioned deficiencies and inadequacies. Even though the above cited methods for dialysis systems meets some of the needs of the market, a combination kidney and liver dialysis system helps remove uremic toxins, hepatic toxins, water, and other impurities from the blood is still desired.

SUMMARY OF THE INVENTION

The present invention is directed to a combination kidney and liver dialysis system and method helps treat multiple organ dysfunction syndrome (MODS) by combining several important dialytic processes such as hemodialysis, hemoperfusion, CRRT (CVVH, CVVHD, CVVHDF, SLED), hemodiafiltration, plasmapheresis, albumin dialysis and lipid dialysis. Via these dialysis processes and techniques the patient's blood will be going through combination and permutations of plasma separation, dilution of blood and ultrafiltration. Thereby, diluting the blood, separating the blood into its plasma and cellular portions, returning the cellular portion to the body, and passing the plasma portion through multiple strategically placed semi-permeable membranes and absorptive surfaces.

One objective of the present invention is to reduce dead space in the dialysis process by separating blood into the cellular portion and the plasma portion.

Another objective is to reduce blood recirculation by using a first entry point and a second entry point in the body for circulating the blood through the hemodialysis device.

Another objective is to increase convective forces.

Yet another objective is to increase the free serum concentration of protein-bound toxins.

Yet another objective is to introduce a large volume of specified replacement fluids infused at specified steps (and later removed to maintain I/O) in order to manipulate and change the equilibrium that exists between the protein-bound toxins and their free serum concentration. This favors increased free serum concentration which will allow the more efficient dialysis removal of these important toxins.

Yet another objective is to increase the internal filtration.

Yet another objective is to introduce modified albumin dialysis.

Yet another objective is to improve temperature/pH dialysis.

Yet another objective is to reduce platelet activation.

Yet another objective is to reduce WBC activation.

Yet another objective is to introduce the novel lipid dialysis (optional).

Yet another objective is to enable lower blood flow rates (QB).

Yet another objective is to introduce a modified dialysate containing charcoal and resins.

Yet another objective is to avoid intubation during dialysis. (optional)

Yet another objective is to avoid ventilator associated complications.

Yet another objective is to avoid oxygen toxicity to the lungs.

Yet another objective is to provide cost effective dialysis for treatment of liver and kidney problems.

In one possible embodiment, the combination kidney and liver dialysis system helps remove uremic toxins, as well as hard to dialyze hepatic toxins, water, and other impurities from the blood. The system utilizes a unique combinations of dialysis processes most importantly the plasmapheresis which involves separating the blood into its plasma portion and cellular portion. Then immediately returning the cellular portion to the body, (optional to run this portion through an (ECMO) extracorporeal membrane oxygenation membrane for oxygenation) diluting the plasma portion with replacement fluids, and then manipulating the plasma portion of the blood to pass through hemoperfusion membranes, hemodiafiltration membranes before going through other processes such as hemoperfusion. Furthermore, dialysis is performed on the plasma portion of the blood with an albumin dialyzer against an albumin dialysate and a high molecular weight cut off (HMWCO) membrane, which is optional. Dialysis is also performed on the plasma portion of the blood with a lipid dialysate comprising 10-30% lipid composition, and a high flux dialyzer, which is optional.

In some embodiments, the system may utilize a portable, lightweight hemodialysis device, hereafter, "device". The device is battery operated. The device utilizes tubing to connect to the patient and to a disposable cassette that contains the means for processing the blood. A simple user interface enables operation of the device and monitoring of blood temperature and pressure.

In one embodiment, the device comprises a pump to carry the blood to and from the body. The pump is configured to pump the blood through the device, and to and from the body of the patient. In one possible embodiment, the blood is pumped at 25-300 ml/min from a first entry point. The first entry point may include the arterial port of HD access or a single lumen access.

The device may further include several replacement fluid mixers. The replacement fluid mixers dilute the plasma portion or whole blood from 1:1 to 4:1 ratio. This additional volume will be removed via ultrafiltration or dialfiltration before the blood or plasma portion is returned to the patient to keep I/O balanced. In one embodiment, after being pumped out of the body, the blood is diluted at a 1:1 or 4:1 ratio with a first replacement fluid. The dilution of the blood is efficacious for reducing anticoagulation need.

In some embodiments, the device includes a membrane plasma separator. The membrane plasma separator serves to separate the blood leaving the body of the patient into a cellular portion and a plasma portion. The cellular portion is immediately deviated from the system and back to the body to create more efficient processing of the plasma portion of the blood. Those skilled in the art will recognize that the cellular portion comprises red blood cells, white blood cells, and platelets. The plasma portion comprises water, blood serum, and various dissolved blood proteins.

In some embodiments, the device includes a high flux dialyzer. The high flux dialyzer utilizes a dialysate consisting of a zero calcium bath to reduce plasma calcium and make the plasma portion of the blood anticoagulated or less coagulable. This is optional. The zero calcium dialysate of the high flux dialyzer enables all dialyzable toxins to be removed for increasing efficiency of the other membranes and dialyzers in the device. This is optional. In one embodiment, the well dialyzed plasma portion is diluted in 1:1 to 4:1 ratio by a second replacement fluid before entering the next segment of the device.

In some embodiments, the device includes one or more hemodiafiltration membranes disposed in series. The hemodiafiltration of the pre-diluted plasma portion occurs via a first hemofilter and a second hemofilter. The two hemofilters may be configured to be densely packed and have a short length and high intra-fiber diameters ratio. The hemofilters have an internal diameter as low as one hundred-twenty microns since there is no cellular component. The two hemofilters may be connected in series while performing the hemodiafiltration and hemofiltration functions.

In some embodiments, the device includes a hemoperfusion membrane. The hemoperfusion may occur via a dialyzer with a HMWCO membrane against a dialysate solution in a container containing suspension of activated charcoal and polystyrene sulfonate and other resins. The output of this hemoperfusion is diluted with a third replacement fluid, such as pre-filter dilution in a 1:1 to 4:1 ratio. This portion can also be performed by passing the plasma portion through hemoperfusion cartridges available. The plasma will come in direct contact with the activated charcoals and resins.

The device further includes an albumin dialyzer that utilizes an albumin dialysate. The albumin dialysate includes at least one of the following: an albumin, an activated charcoal, a polystyrene sulfonate, and a resin or anion exchanger. The output of the hemodiafiltration of the plasma portion passes through the albumin dialyzer.

In some embodiments, the albumin dialyzer utilizes a high molecular weight cut off (HMWCO) membrane, whereby the plasma portion flows through the high molecular weight cut off membrane and the albumin dialysate flows on the opposite side of this membrane. This albumin dialysate is in a closed system of albumin dialysate consisting of either a pure portion of a large reservoir of 5% albumin or several liters of 5% albumin plus activated charcoal and polystyrene sulfonate. This is optional. This remaining suspension may be warmed through a warming device and cooled through a cooling device, such that the albumin that is diluted secondary to the ultrafiltration formed returns to the reservoir in a concentrated form.

In some embodiments, the device includes a lipid dialyzer that utilizes a lipid dialysate to further purify the plasma portion. The lipid dialysate may include about 10% to 30% lipids or oils, such as intralipid that is used for intravenous parenteral nutrition. In one embodiment, the plasma portion is dialyzed against the lipid dialysate after passing through the high molecular weight cut off membrane of the albumin dialyzer. This is optional.

In some embodiments, the device may include an extracorporeal membrane oxygenation membrane (ECMO). The extracorporeal membrane oxygenation membrane is configured to oxygenate the cellular portion of the blood before reentering the body. The output of this combined albumin and lipid dialysis is returned to patient via a different blood access, such as a single lumen, placed in the opposing limb, combining with the plasma portion and reconstitute the whole blood as it enters the patient. This is for an optional Lipid and/or Albumin dialysis.

Further, the device may include a user interface for monitoring I/O and net volume of blood circulating through the device, venous and arterial pressures, blood flows, dialysate flows, U/F rates, oxygen saturation etc. The user interface may be adjusted with the replacement fluid. In additional embodiments, volume is monitored and adjusted with all replacement fluid, and a filter may be introduced for safety to trap any carbon/particulate matter and remove the carbon/particulate matter from the cellular portion before reentering the patient as well as air bubbles. The device may further include a bubble trap, a charcoal trap, and various filters for safely trapping any carbon/particulate matter and removing it from the cellular portion of the blood before reentering the patient. Furthermore, many important sensors required in CRRT and HD are placed appropriately.

The method for treating multiple organ dysfunction syndrome (MODS) by dialyzing the blood for the kidney and liver includes diluting the blood, separating the blood into plasma and cellular portions, returning the cellular portion to the body, and passing the plasma portion through multiple strategically placed semi-permeable membranes and absorptive surfaces comprises an initial Step of pumping the blood from the body of a patient.

Another Step may include adding a first replacement fluid to the blood. A next Step comprises passing the blood through a high flux dialyzer, the high flux dialyzer comprising a zero calcium dialysate. The method may include a Step of separating the blood into a plasma portion and a cellular portion. A Step comprises returning the cellular portion of the blood to the body upon separation of the blood.

The method may further include a Step of adding a second replacement fluid to the plasma portion of the blood. An additional Step includes passing the plasma portion through a plurality of hemodiafiltration membranes. A further Step comprises passing the plasma portion through a hemoperfusion membrane. The method may further include a Step of adding a third replacement fluid to the plasma portion of the blood.

The method may further include dialyzing the plasma portion of the blood through an albumin dialyzer, the albumin dialyzer comprising a high molecular weight cut off membrane and an albumin dialysate, the albumin dialysate comprising at least one of the following: an albumin, an activated charcoal, a polystyrene sulfonate, and a resin.

In some embodiments, the method may include dialyzing the plasma portion against a lipid dialysate, the lipid dialysate comprising various percent of lipids or oils by weight or volume (i.e., about 10% to 30% lipids or oils). An additional Step may include passing the cellular portion through an extracorporeal membrane oxygenation membrane (ECMO), the extracorporeal membrane oxygenation membrane configured to oxygenate the cellular portion. A final Step comprises returning the plasma portion to the body of the patient.

Other systems, devices, methods, features, and advantages will be or become apparent to one with skill in the art upon examination of the following drawings and detailed description. It is intended that all such additional systems, methods, features, and advantages be included within this description, be within the scope of the present disclosure, and be protected by the accompanying claims and drawings.

BRIEF DESCRIPTION OF THE DRAWINGS

The invention will now be described, by way of example, with reference to the accompanying drawings, in which.

Like reference numerals refer to like parts throughout the various views of the drawings.

DETAILED DESCRIPTION OF THE INVENTION

Figure 1:
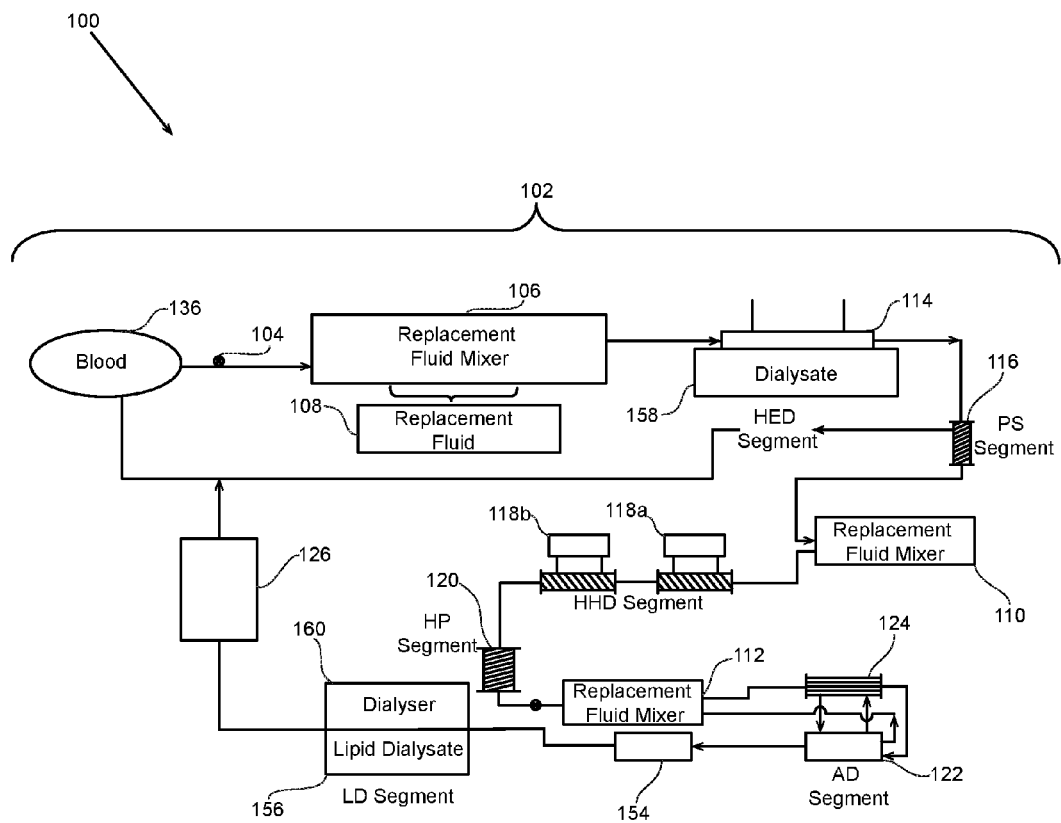
FIG. 1 illustrates a block diagram of an exemplary combination kidney and liver dialysis system with a high flux dialyzer positioned before a membrane plasma separator, in accordance with an embodiment of the present invention.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "first," "second," "left," "rear," "right," "front," "vertical," "horizontal," and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

At the outset, it should be clearly understood that like reference numerals are intended to identify the same structural elements, portions, or surfaces consistently throughout the several drawing figures, as may be further described or explained by the entire written specification of which this detailed description is an integral part. The drawings are intended to be read together with the specification and are to be construed as a portion of the entire "written description" of this invention as required by 35 U.S.C. § 112.

In one embodiment of the present invention presented in FIGS. 1-9B, a combination kidney and liver dialysis system 100 and method 200 helps treat multiple organ dysfunction syndrome (MODS) through several unique combinations and permutations of several important dialysis processes. The combination kidney and liver dialysis system 100 and method 200 includes the separation of the whole blood from a patient into its major components before going through a series of different forms of diffusive, convective and absorptive processes, including: diffusive, convective as well as adsorptive in hemoperfusion and combination of diffusive and convective processes in CRRT, hemodialysis, hemodiafiltration, hemoperfusion, albumin dialysis, and lipid dialysis.

In one possible embodiment, the combination kidney and liver dialysis system 100 provides a portable, lightweight hemodialysis device 102 that helps remove uremic toxins, hepatic toxins, water, and other impurities from the blood through a unique process involving separating the blood into a plasma portion and a cellular portion, immediately returning the cellular portion to the body 136, diluting the plasma portion with replacement fluids, and then manipulating the plasma portion to pass through a hemoperfusion membrane 120, a plurality of hemodiafiltration membranes 118a, 118b, and an extracorporeal membrane oxygenation membrane 126. Furthermore, the device provides dialysis that is performed on the plasma portion with an albumin dialyzer 122 against an albumin dialysate 154 and a high molecular weight cut off membrane 124. Dialysis is also performed on the plasma portion with a lipid dialyzer 124 against a lipid dialysate 156 comprising 10-30% lipid composition, and a high flux dialyzer 114.

Those skilled in the art will recognize that the combination kidney and liver dialysis system 100 and method 200 increases the efficiency of standard dialysis while also increasing the free serum concentration of "protein-bound toxins". This may effectively improve the inefficiency of dialysis for the kidney and more so for the liver and form the basis for kidney and liver dialysis. Using the system 100 and method 200 early in the series of steps of manipulating the blood will increase efficiency by removing the cellular components that occupy about 40% of the volume that comes in contact with a series of membranes and resins/charcoal that act as "dead space" which reduces the efficiency of any diffusive, convective or absorptive processes by that much.

As shown in FIG. 1, the system 100 may include a portable, lightweight hemodialysis device 102, hereafter, "device 102". The device 102 utilizes tubing to connect to the patient and to a disposable cassette that contains the means for processing the blood. A simple user interface enables operation of the device 102 and monitoring of blood temperature and pressure. A battery may be used to power the device 102.

In one embodiment, the device 102 comprises at least one pump 104 that is configured to force the blood to and from the body 136. In one embodiment, the pump 104 is configured to pump 104 the blood from a first access point 138 of the body, through the device 102, and finally return the blood to a second entry point in the body 136. In one possible embodiment, the blood is pumped at 25-400 ml/min from a first access point 138. The first access point 138 may include the arterial port of HD access or a single lumen access from a limb. It is significant to note that there are several other pumps filters, sensors and traps commonly used in different dialysis modalities.

In some embodiments, the device 102 may include at least one replacement fluid mixer 106. The replacement fluid mixers 106 dilute the blood and or plasma with an appropriate replacement fluid in 1:1 to 4:1 ratios. The replacement fluid mixer 106 introduces large volumes of specified replacement fluids 108, 110, 112 infused at specified steps in order to dilute and ultimately manipulate and change the equilibrium that exists between the protein-bound toxins and their free serum concentration. This favors increased free serum concentration of hard to dialyze toxins that are mainly protein-bound which will allow the more efficient dialysis removal of these important toxins.

In one exemplary use of the pump 104 and replacement fluid mixer 106, the blood is pumped out of the body 136 from the first access point 138, such as a left arm. After being pumped out of the body 136, the blood is diluted at a 1:1 or 4:1 ratio with a first replacement fluid 108. The first replacement fluid 108 may include a mixture consisting of 3 amps of bicarbonate in 1 liter of D5W. The dilution of the blood with the first replacement fluid 108 is efficacious for reducing anticoagulation. In one alternative embodiment, blood heparinization occurs during the dilution if needed.

In some embodiments, the device 102 may include a membrane plasma separator 116. The membrane plasma separator 116 serves to separate the blood leaving the body 136 of the patient into a cellular portion and a plasma portion. The cellular portion is immediately deviated from the system and back to the body to create more efficient processing of the plasma portion of the blood with option of being oxygenated via ECMO before returning to the patient. The membrane plasma separator 116 may create an output consisting of a 2:1 ratio of plasma portion to cellular portion volume. Those skilled in the art will recognize that the cellular portion comprises mostly red blood cells, white blood cells, and platelets in small plasma volume. The plasma portion comprises water, electrolytes, blood serum, and various dissolved blood proteins.

In some embodiments, the device 102 includes a high flux dialyzer 114. The high flux dialyzer 114 utilizes a dialysate 158 consisting of a zero calcium bath to reduce plasma calcium and make the plasma portion of the blood coagulable. The low including zero calcium dialysate 158 of the high flux dialyzer 114 enables all dialyzable toxins to be removed for increasing efficiency of the other membranes and dialyzers in the device 102. In one embodiment, the dialyzed plasma portion is diluted in 1:1 to 4:1 ratio by a second replacement fluid 110 before entering the next segment of the device 102.

Figure 2:
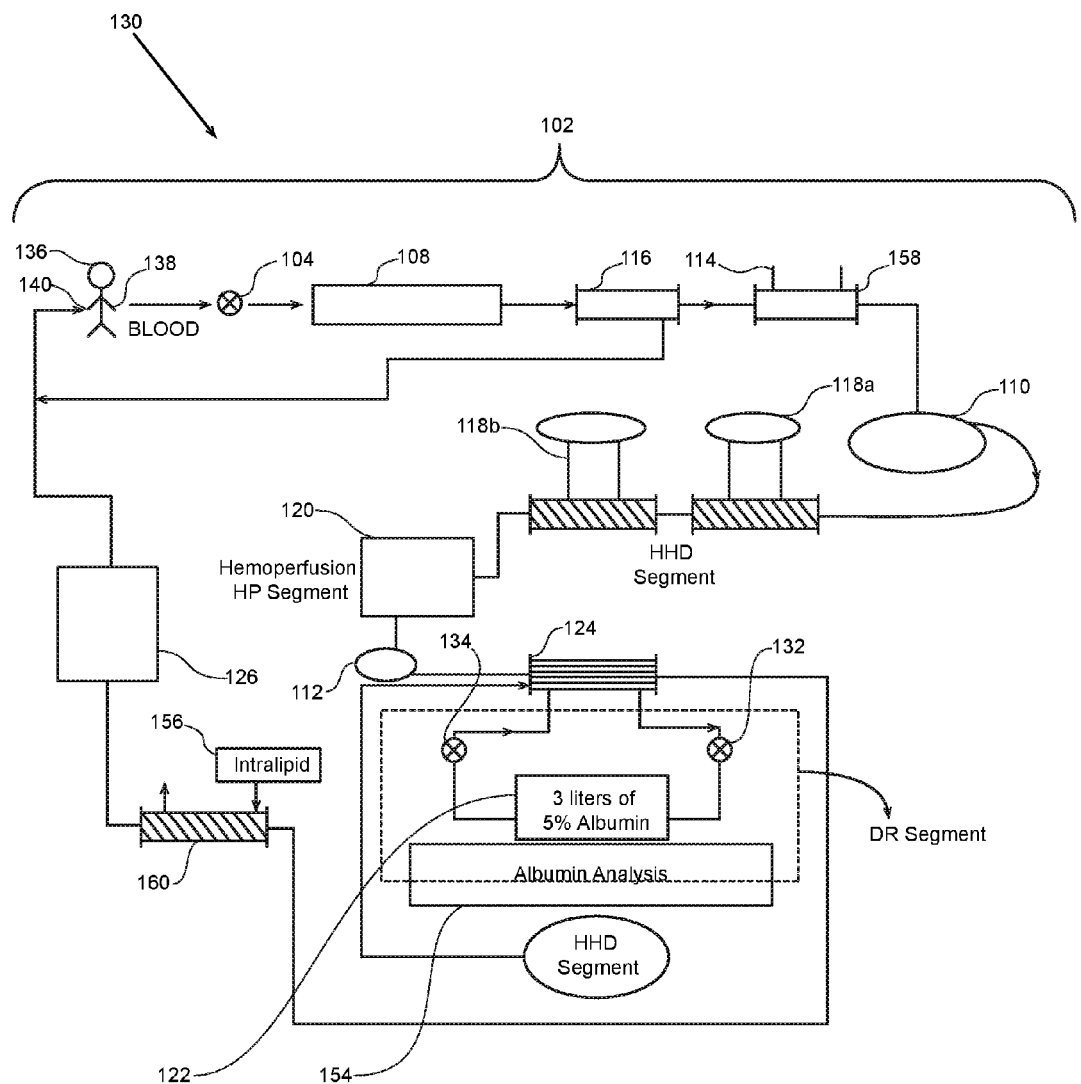
FIG. 2 illustrates a block diagram of a second embodiment of an exemplary combination kidney and liver dialysis system with a membrane plasma separator positioned before a high flux dialyzer, in accordance with an embodiment of the present invention.

One alternative embodiment of a system 130, as illustrated in FIG. 2, is arranged such that the membrane plasma separator 116 positions before the high flux dialyzer 114. Though the other components between the two systems 100, 130 are substantially the same. By arranging the membrane plasma separator 116 before the high flux dialyzer 114, only the plasma portion receives dialysis from the zero calcium dialysate 158. The calcium dialyzer 114 is optional, since heparinization may be used; whereas the cellular portion returns to the body 136 with no further processing.

In some embodiments, the device 102 includes a plurality of hemodiafiltration membranes 118a, 118b disposed in series. The hemodiafiltration will be used to perform CRRT, CVVH, CVVHD, CVVHDF with regional citrated or heparinization. This hemodiafiltraion of the pre-diluted plasma portion occurs via a first hemofilter 118a and a second hemofilter 118b. The two hemofilters 118a, 118b are configured to be densely packed and have a short length and high intra-fiber diameters ratio. The hemofilters 118a, 118b have an internal diameter as low as one hundred-twenty microns since there is no cellular component in order to increase the internal filtration.

The two hemofilters 118a, 118b may be connected in series while performing the hemodiafiltration and hemofiltration functions. In one embodiment, the first hemofilter 118a will have no dialysate to improve the filtration while the second hemofilter 118b has a resin/charcoal dialysate disposed in a closed loop system. The dialysate used in the hemodiafiltration membranes 118a, 118b run countercurrent to the blood flow. It is significant to note that a substantial portion of the replacement fluid will be removed via ultrafiltration at this point.

In some embodiments, the device 102 includes a hemoperfusion membrane 120. The hemoperfusion through the hemoperfusion membrane 120 may occur via a container containing suspension of activated charcoal, polystyrene sulfonate, and other resins. In operation, the plasma portion from the second hemofilter 118b passes through the hemoperfusion membrane 120 which contains a suspension of activated charcoal (260 g) and polystyrene sulfonate (140 g). The plasma portion comes in close contact with the charcoal and resin. The plasma portion flows from a bottom end towards a top end of the hemoperfusion membrane 120 and is transferred to the next segment of the device 102. This directional flow may help avoid caking of the charcoal and resin. In one embodiment, the output from the hemoperfusion membrane 120 is diluted with a third replacement fluid 112, such as pre-filter dilution, in a 2:1 ratio.

The device 102 further includes an albumin dialyzer 122 containing an albumin dialysate 154. The albumin dialysate 154 includes at least one of the following: an albumin, an activated charcoal, a polystyrene sulfonate, and a resin. The plasma portion output from the hemodiafiltration membranes 118a, 118b and hemoperfusion membrane 120 passes through the albumin dialyzer 122.

In some embodiments, the albumin dialyzer 122 utilizes a high molecular weight cut off membrane 124, whereby the plasma portion flows through the high molecular weight cut off membrane 124 and the albumin dialysate 154 flows on the opposite side of the high molecular weight cut off membrane 124. The high molecular weight cut off membrane 124 comprises a molecular weight cut-off point (MWCO). Those skilled in the art will recognize that the HMWCO should be chosen as high as possible in order to maximize the dialysis rate of larger molecules/toxins. However, in order to achieve a higher sample recovery the HMWCO may be about half of the molecular weight of the plasma portion of the blood.

After passing through the high molecular weight cut off membrane 124, the plasma portion is dialyzed against a closed system of albumin dialysate 154. In one embodiment, the albumin dialysate 154 consists of either a pure solution of a 3 liter reservoir of 5% albumin, or a solution of this 5% albumin with activated charcoal, polystyrene sulfonate, and resins. In one alternative embodiment, the albumin dialysate 154 plus activated charcoal, polystyrene sulfonate, and resin suspension passes through the high flux dialyzer 114. This additional passage through the high flux dialyzer 114 enables the formation of ultrafiltration, which is then discarded. It is significant to note that this blood flow path and passage of the blood and plasma will need to be designed to have appropriate sensors, filters, traps and monitors.

In some embodiments, this remaining suspension may be warmed through a warming device 132 and cooled through a cooling device 134, such that the albumin that is diluted secondary to the ultrafiltration formed returns to the reservoir in a concentrated form. The warming device 132 is configured to warm the plasma portion to about 42° Celsius, after passing through the albumin dialyzer 122. The cooling device 134 is configured to warm the plasma portion up to 35° Celsius, after passing through the albumin dialyzer 122.

In some embodiments, the device 102 includes a lipid dialyzer 160 that utilizes a lipid dialysate 156 to further purify the plasma portion. The lipid dialysate 156 may include about 10% to 30% lipids or oils, such as intralipids and lipid components used in total parenteral nutrition. In one embodiment, the plasma portion is dialyzed against the lipid dialysate 156 after passing through the high molecular weight cut off membrane 124 of the albumin dialyzer 122.

In some embodiments, the device 102 may include an extracorporeal membrane oxygenation membrane (ECMO) 126. The extracorporeal membrane oxygenation membrane 126 is configured to oxygenate the plasma portion of the blood before reentering the body 136. The blood is pumped back into the body 136 at a second access point 140, such as a right arm. It is significant to note that the use of two access points 138, 140 reduces any if not excessive recirculation of blood which leads to inefficient dialysis.

The output plasma portion of the combined albumin and lipid dialyzers 122, 160, and the extracorporeal membrane oxygenation membrane 126 is returned to patient via a second access point 140 (single lumen), which is placed in the opposing limb of the first access point 138. In this manner the plasma portion is combined with the cellular portion to reconstitute the whole blood as it enters the body 136 of the patient.

Further, the device 102 may include a user interface (not shown) for monitoring I/O and net volume of blood circulating through the device 102 and other important and vital functions that are regularly monitored through CRRT and other forms of dialysis. The user interface may be adjusted with the at least one replacement fluid 108, 110, 112. In additional embodiments, volume is monitored and adjusted with the at least one replacement fluid 108, 110, 112, and a filter may be introduced for safety to trap any carbon/particulate matter and remove the carbon/particulate matter from the cellular portion before reentering the patient. The device 102 may further include a bubble trap, a charcoal trap, and various filters, sensors and monitors for safely trapping any carbon/particulate matter and removing it from the cellular portion of the blood before reentering the patient.

Figure 3:
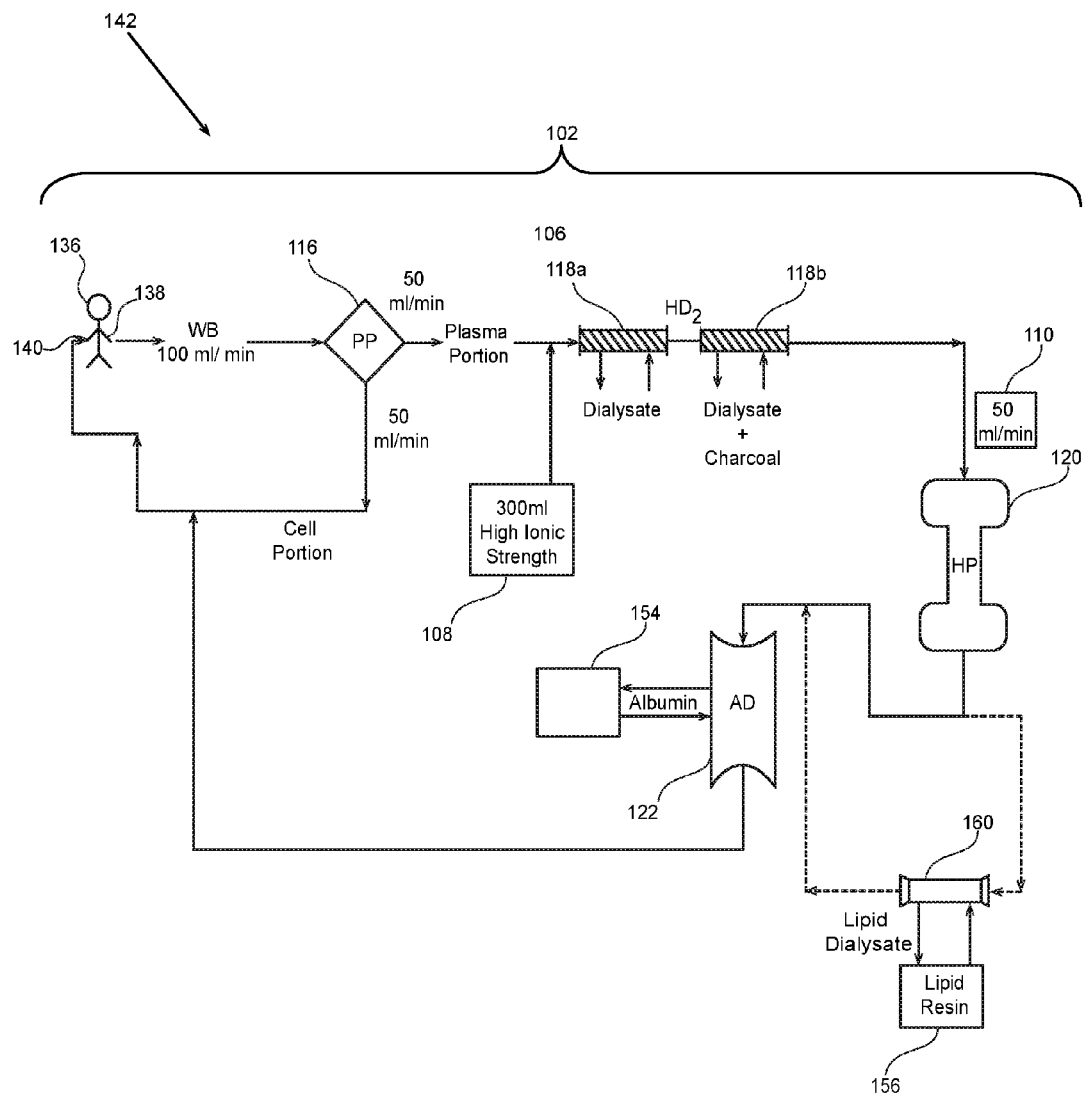
FIG. 3 illustrates a block diagram of a third embodiment of an exemplary combination kidney and liver dialysis system, in accordance with an embodiment of the present invention.

It is significant to note that the components of the system 100 may be arranged in myriad combinations and sequences. The components are easily attached, detached, and rearranged in the closed loop system of the present invention. For example, FIG. 3 illustrates a block diagram of a third embodiment of a combination kidney and liver dialysis system 142. In this embodiment, the first replacement fluid 108 is a composed of a high ionic solution. The lipid dialyzer is also optional in the system 142.

Figure 4:
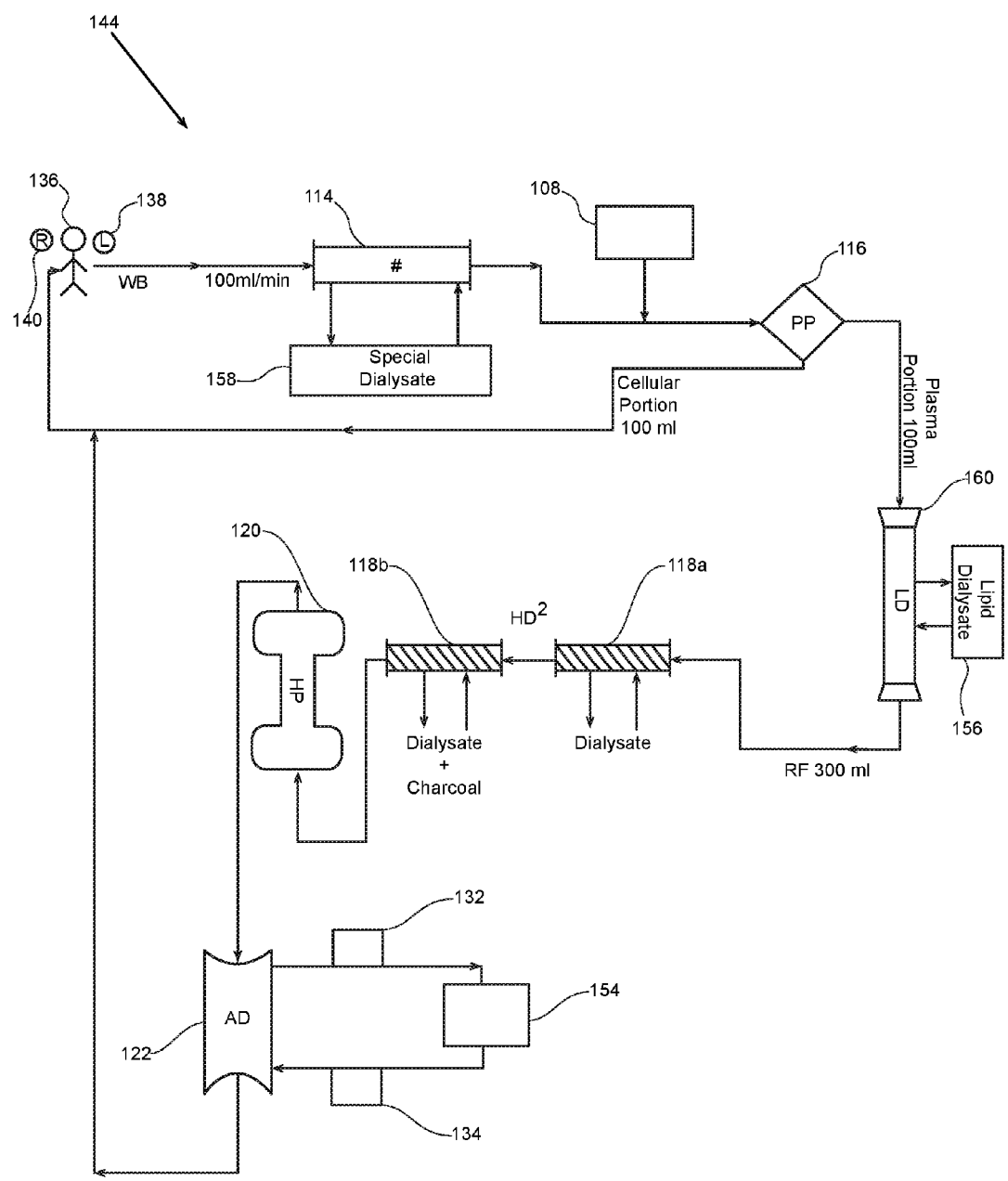
FIG. 4 illustrates a block diagram of a fourth embodiment of an exemplary combination kidney and liver dialysis system, in accordance with an embodiment of the present invention.
Figure 5:
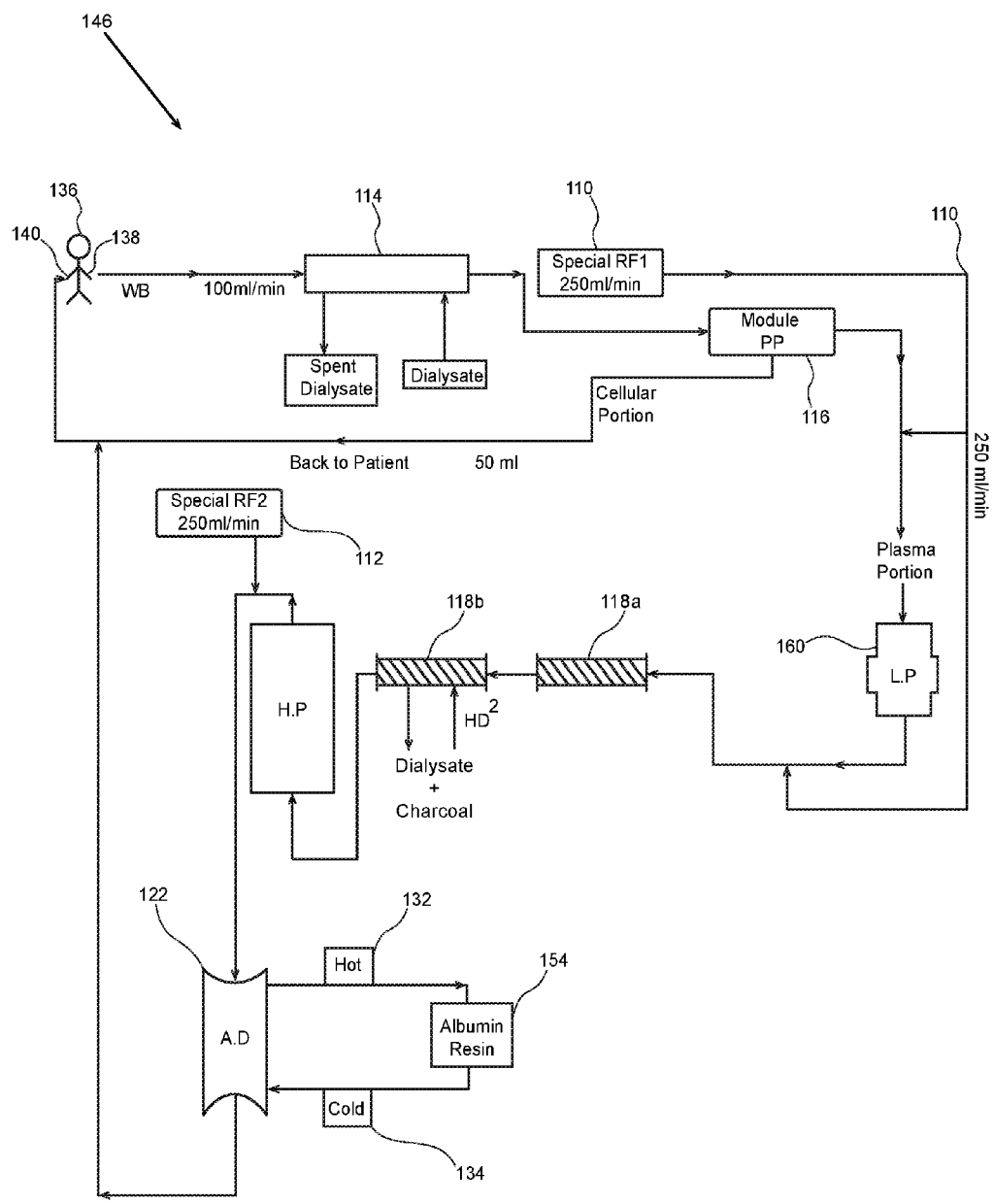
FIG. 5 illustrates a block diagram of a fifth embodiment of an exemplary combination kidney and liver dialysis system, in accordance with an embodiment of the present invention.

In another example, FIG. 4 illustrates a fourth embodiment of a combination kidney and liver dialysis system 144. In this embodiment, the lipid dialyzer positions before the hemodiafiltration filters. FIG. 5 illustrates a block diagram of a fifth embodiment of an exemplary combination kidney and liver dialysis system 146. In this embodiment, the concentration of the first replacement fluid 108 maybe increased to higher volume of a high ionic solution.

Figure 6:
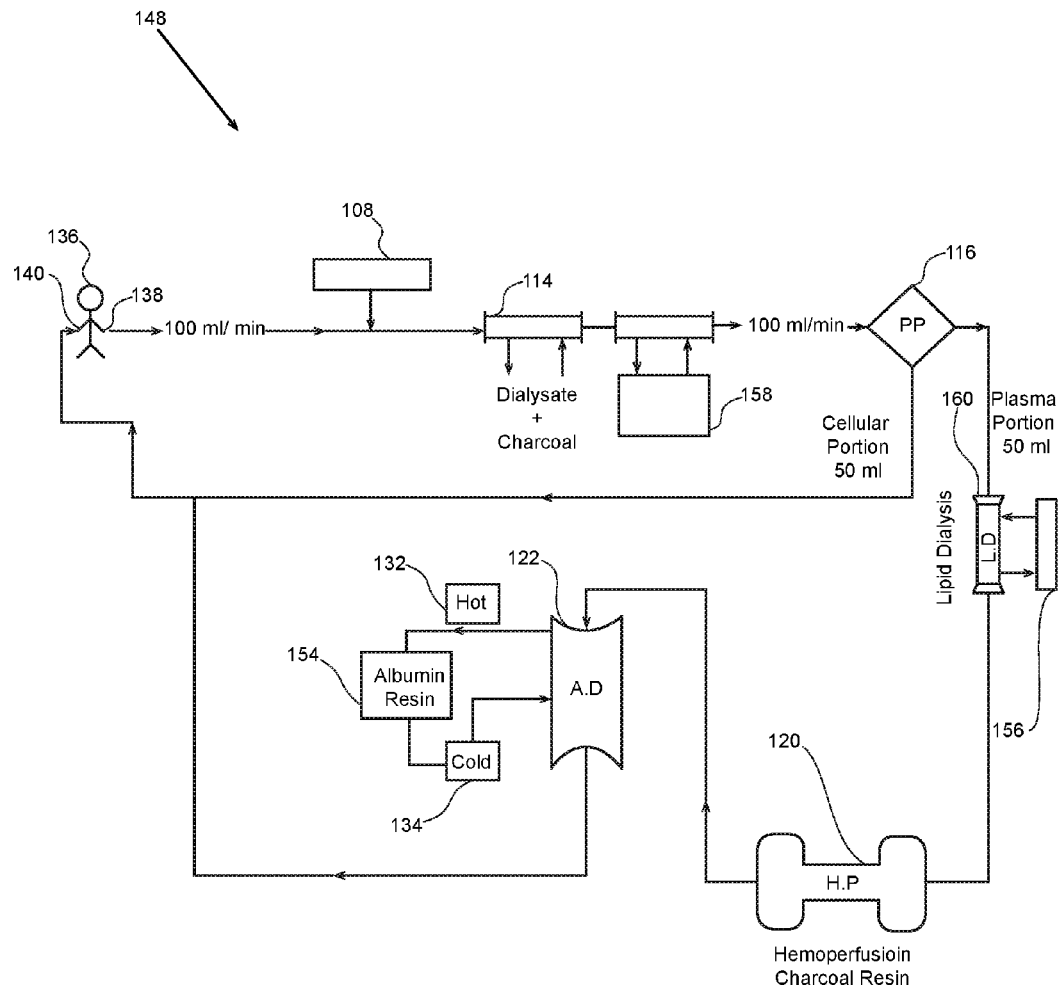
FIG. 6 illustrates a block diagram of a sixth embodiment of an exemplary combination kidney and liver dialysis system, in accordance with an embodiment of the present invention.
Figure 7:
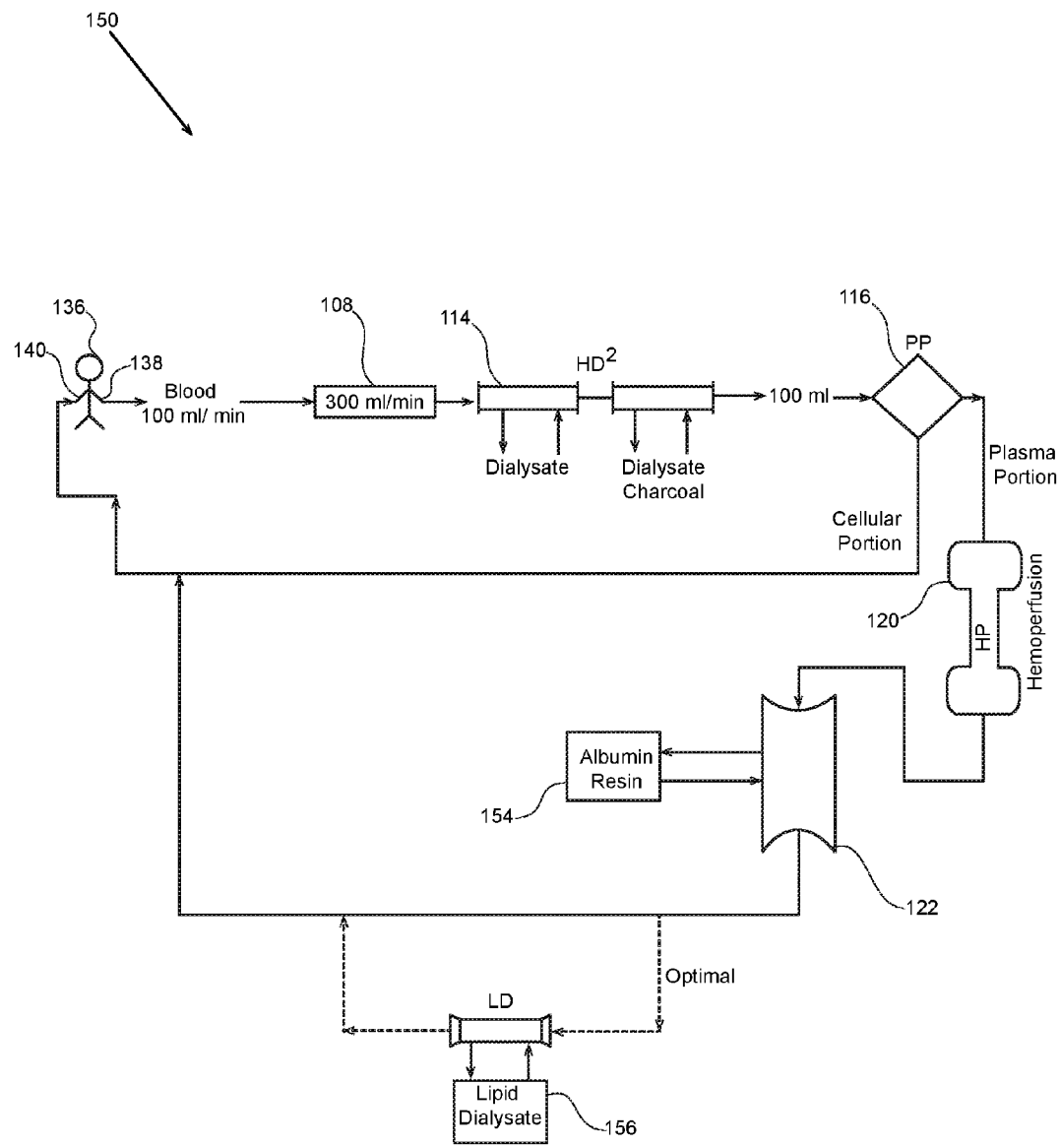
FIG. 7 illustrates a block diagram of a seventh embodiment of an exemplary combination kidney and liver dialysis system, in accordance with an embodiment of the present invention.

In yet further alternative embodiments, FIG. 6 illustrates a block diagram of a sixth embodiment of an exemplary combination kidney and liver dialysis system 148. In this embodiment, the plurality of hemodiafiltration membranes 118a, 118b are not used. FIG. 7 illustrates a block diagram of a seventh embodiment of an exemplary combination kidney and liver dialysis system 150. In this embodiment, the lipid dialyzer 160 is optional, and when used, positions after the albumin dialyzer 122.

Figure 8:
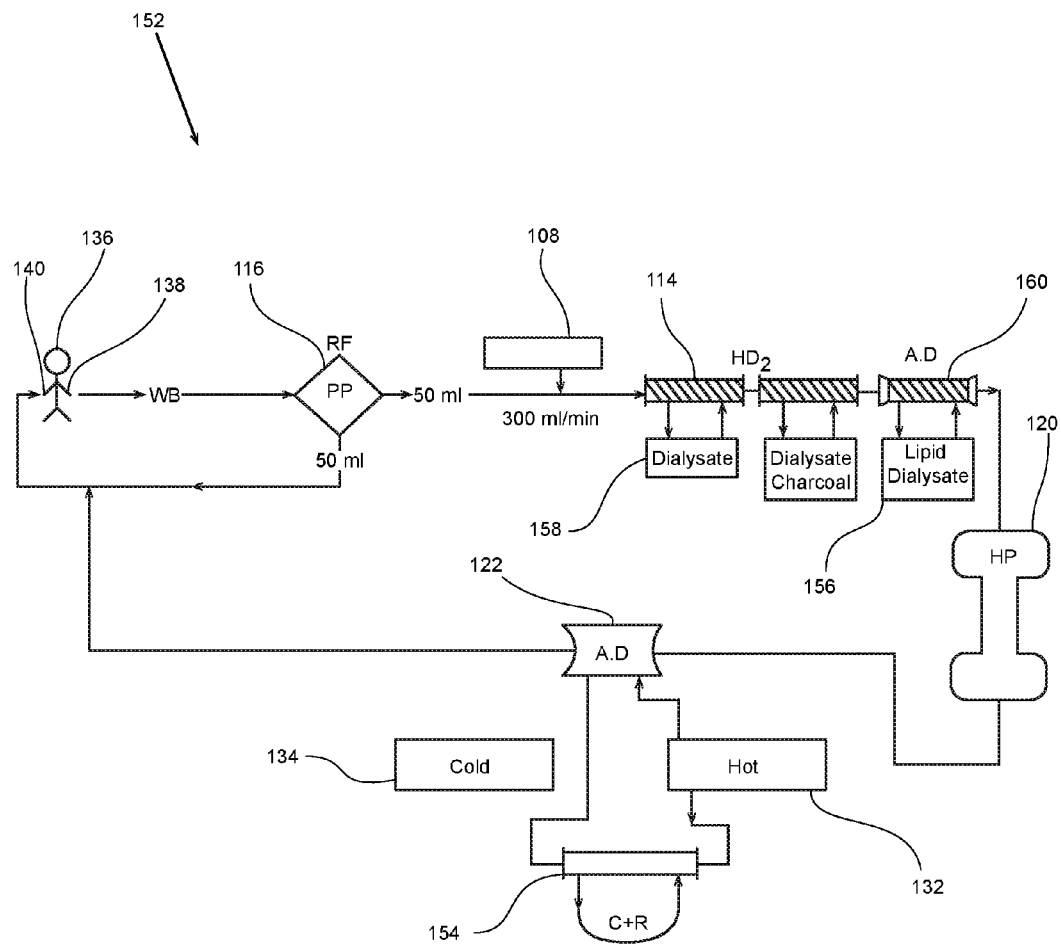
FIG. 8 illustrates a block diagram of an eighth embodiment of an exemplary combination kidney and liver dialysis system, in accordance with an embodiment of the present invention.

FIG. 8 illustrates a block diagram of an eighth embodiment of an exemplary combination kidney and liver dialysis system 152. In this embodiment, the hemoperfusion membrane 120 positions between the lipid dialyzer 160 and the albumin dialyzer 122. In any case, the general functions of separating the blood components, adding large volumes of replacement fluids, passing the plasma portion of the blood through various semi-permeable membranes, and utilizing lipid and albumin dialyzers 160, 122 remains substantially the same.

Thus, the device 102 utilizes various semi-permeable membranes, absorbers and dialyzers 122, 160 arranged in multiple unique and novel sequences to increase efficiency of kidney dialysis as well as liver toxin removal while also oxygenating the blood: a) Reducing recirculation through the use of two oppositely disposed access points on the body 136, each access point located in a different limb, to decrease recirculation entirely; b) Reducing dead-space, after plasmapheresis mostly the plasma is occupying the precious membrane surface area so crucial for the dialysis processes; c) Increasing the convective dialysis by increasing both ultrafiltration and internal filtration;

d) Increasing the free serum concentration of the protein-bound toxins via dilution with the at least one replacement fluid to favor the equilibrium towards higher serum concentration of the non-bound toxins—for example, a 1:4 dilution and subsequently a 1:4 dilution forces a change in equilibrium; e) Using specific chemicals to change the equilibrium as well as the temperature of the blood; f) Using an albumin dialyzer 122; g) Using a lipid dialyzer 160; h) Using a combination of albumin, activated charcoal, and resins for specialized albumin based dialysis with an albumin dialyzer 122; and i) Using an ECMO membrane 126 to oxygenate blood before returning to the body 136.

Figure 9:
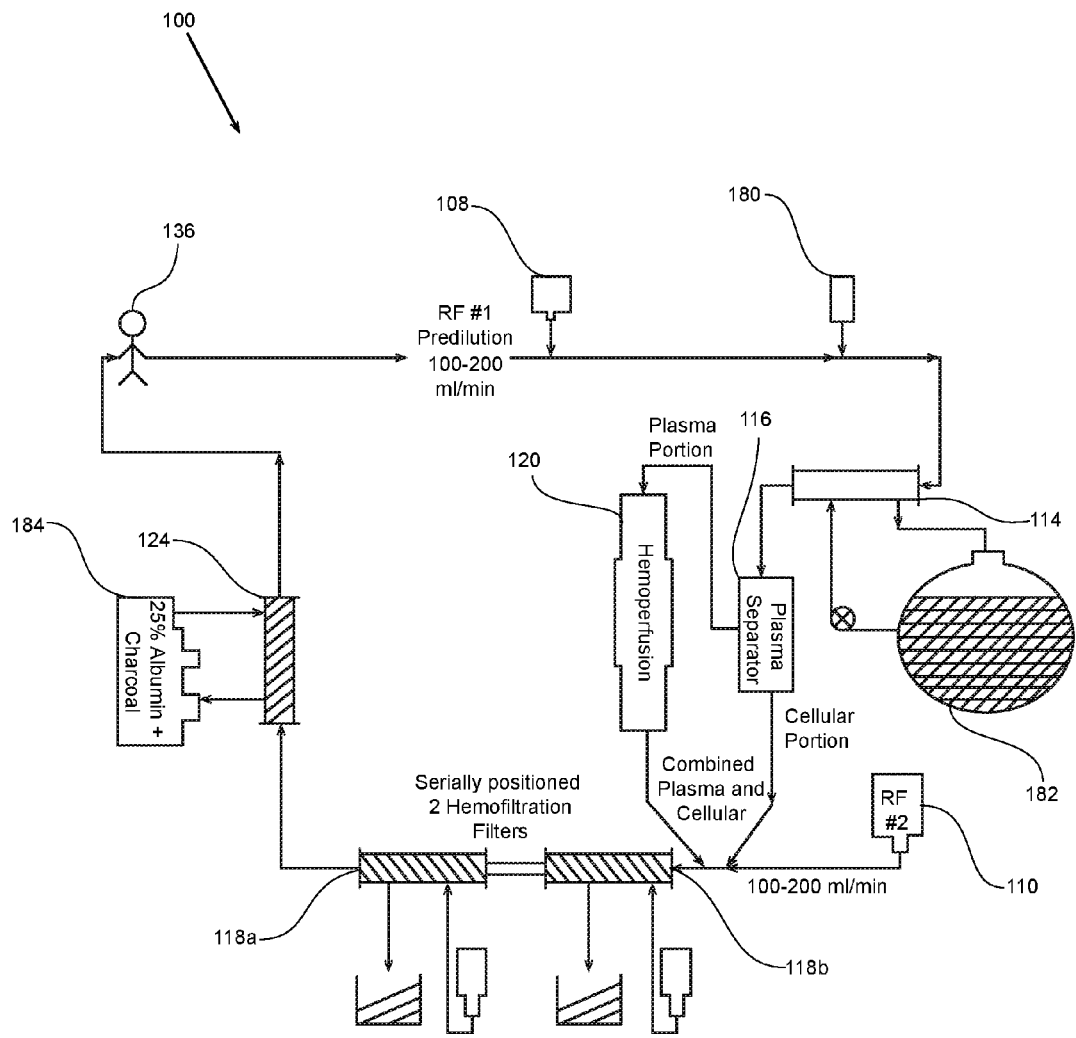
FIG. 9 illustrates a block diagram of a ninth embodiment of an exemplary combination kidney and liver dialysis system, in accordance with an embodiment of the present invention.

FIG. 9 illustrates a block diagram of a ninth embodiment of an exemplary combination kidney and liver dialysis system 162. The system 162 is configured to perform the functions of separating the blood components, adding large volumes of replacement fluids, passing the plasma portion of the blood through various semi-permeable membranes, and utilizing lipid and albumin dialyzers 160, 122.

In one embodiment, the blood passes through a high flux dialyzer 114, the high flux dialyzer 114 comprising a standardized dialysate or specially formulated one to address the electrolyte needs of the patient. The high flux dialyzer 114 utilizes a standard dialysate 158 or one consisting of a zero calcium bath to reduce plasma calcium and make the plasma portion of the blood less coagulable. At this point an anticoagulations fluid 180 may be utilized such as regional citrate or heparinization. Next, the blood passes through a first suspension 182 of charcoal. In one embodiment, the first suspension 182 comprises 260 grams of powder charcoal and 140 grams polystyrene sulfonate.

A plasma separator 116 separates the blood in to a plasma portion and a cellular portion. The plasma portion passes through a hemoperfusion membrane 120 before reuniting with the cellular portion. The blood may then pass through the two hemofilters 118a, 118b. The hemofilters 118a, 118b may be connected in series while performing the hemodiafiltration and hemofiltration functions. Finally, after passing through the high molecular weight membrane 124, a reservoir 184 releases a solution of 25% albumin and charcoal provides filtration for the high molecular weight membrane 124.

Figure 10:
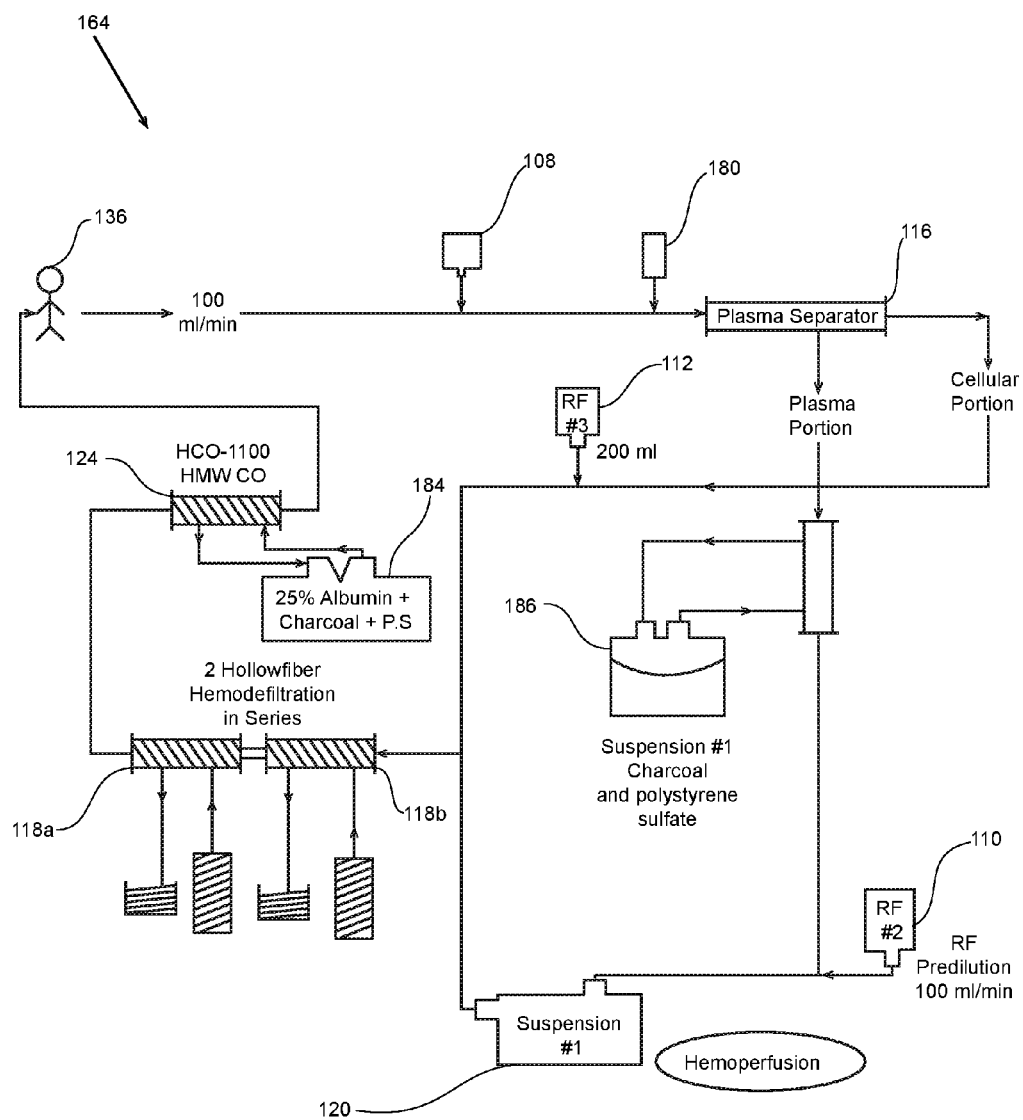
FIG. 10 illustrates a block diagram of a tenth embodiment of an exemplary combination kidney and liver dialysis system, in accordance with an embodiment of the present invention.

FIG. 10 illustrates a block diagram of a tenth embodiment of an exemplary combination kidney and liver dialysis system 164. The system 164 is configured to perform the functions of separating the blood components, adding large volumes of replacement fluids, passing the plasma portion of the blood through various semi-permeable membranes, and utilizing lipid and albumin dialyzers 160, 122. After receiving an anticoagulations fluid 180, such as regional citrate or heparinization, the blood passes through a high flux/high efficiency filter 188. A first solution 186 consisting of 260 grams of powder charcoal and 140 grams polystyrene sulfonate may be added at this point. In one embodiment, at the two hemofilters 118a, 118b, about 24,000 ml of RF is removed, and about 60,000 ml of BF is removed. Further, at the high molecular weight membrane 124, a reservoir 184 releases a solution of 25% albumin and charcoal before recirculating back into the body 136.

Figure 11:
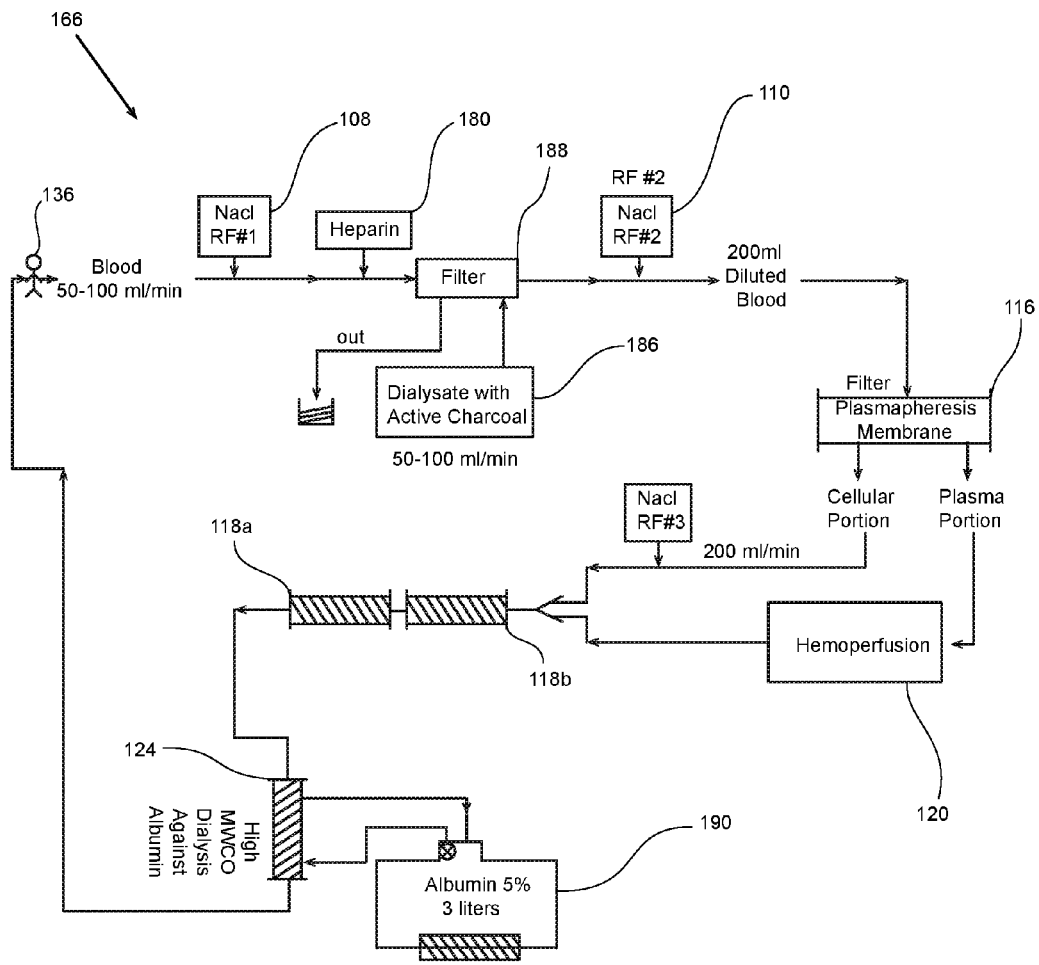
FIG. 11 illustrates a block diagram of an eleventh embodiment of an exemplary combination kidney and liver dialysis system, in accordance with an embodiment of the present invention.

FIG. 11 illustrates a block diagram of an eleventh embodiment of an exemplary combination kidney and liver dialysis system 166. The system 166 is configured to perform the functions of separating the blood components, adding large volumes of replacement fluids, passing the plasma portion of the blood through various semi-permeable membranes, and utilizing lipid and albumin dialyzers 160, 122. After the blood leaves the body 136, a first replacement fluid 108 and an anticoagulation fluid 180 are added, before the blood passes through a high flux/high efficiency filter 188 to provide the first filtration for the blood. Later in the dialysis, hemofilters 118a, 118b may be connected in series while performing the hemodiafiltration and hemofiltration functions. A 5% albumin solution 190 is exchanges fluids with the hemofilters 118a, 118b.

Figure 12:
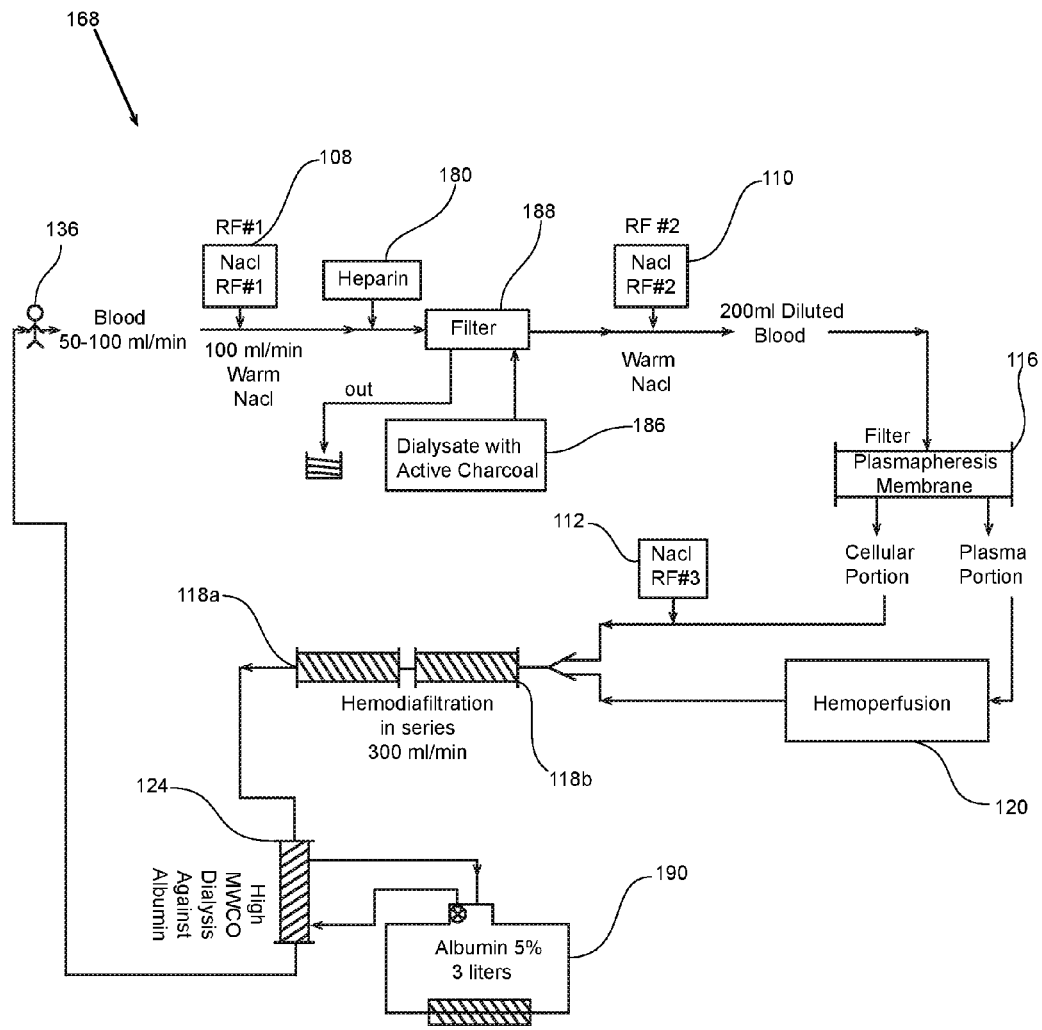
FIG. 12 illustrates a block diagram of a twelfth embodiment of an exemplary combination kidney and liver dialysis system, in accordance with an embodiment of the present invention.

FIG. 12 illustrates a block diagram of a twelfth embodiment of an exemplary combination kidney and liver dialysis system 168. The system 168 is configured to perform the functions of separating the blood components, adding large volumes of replacement fluids, passing the plasma portion of the blood through various semi-permeable membranes, and utilizing lipid and albumin dialyzers 160, 122. After the blood leaves the body, a first replacement fluid 108 and an anticoagulation fluid 180 are added. A high flux/high efficiency filter 188 provides the first filtration for the blood. Then, the blood passes through a plasma separation membrane 116. The cellular portion receives a third replacement fluid 112, while the plasma portion passes through the hemoperfusion membrane 120. A 5% albumin solution 190 is then integrated into the hemofilters 118a, 118b while performing the hemodiafiltration and hemofiltration functions.

Figure 13:
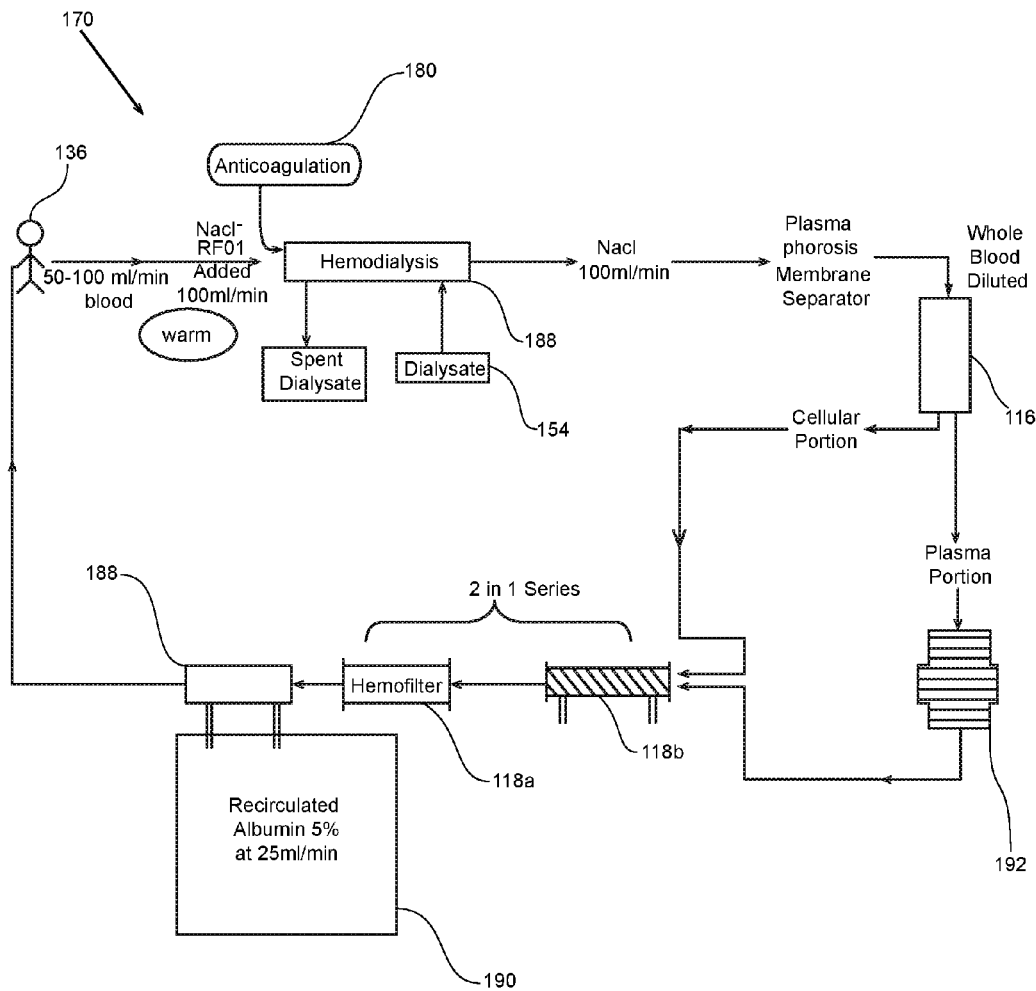
FIG. 13 illustrates a block diagram of a thirteenth embodiment of an exemplary combination kidney and liver dialysis system, in accordance with an embodiment of the present invention.

FIG. 13 illustrates a block diagram of a thirteenth embodiment of an exemplary combination kidney and liver dialysis system 170. The system 170 is configured to perform the functions of separating the blood components, adding large volumes of replacement fluids, passing the plasma portion of the blood through various semi-permeable membranes, and utilizing lipid and albumin dialyzers 160, 122. After the blood leaves the body 136, a dialysate 154 and an anticoagulation fluid 180 are added. A warming device 132 warms the plasma portion of the blood to about 42° Celsius at one or more locations in a circuit/assemblage. After the blood passes through the membrane plasma separator 116, a charcoal and resin filter 192 helps filter the blood. The hemofilters 118a, 118b perform the hemodiafiltration and hemofiltration functions. In this embodiment, a 5% albumin solution 190 is exchanges fluids with the hemofilters 118a, 118b.

Figure 14:
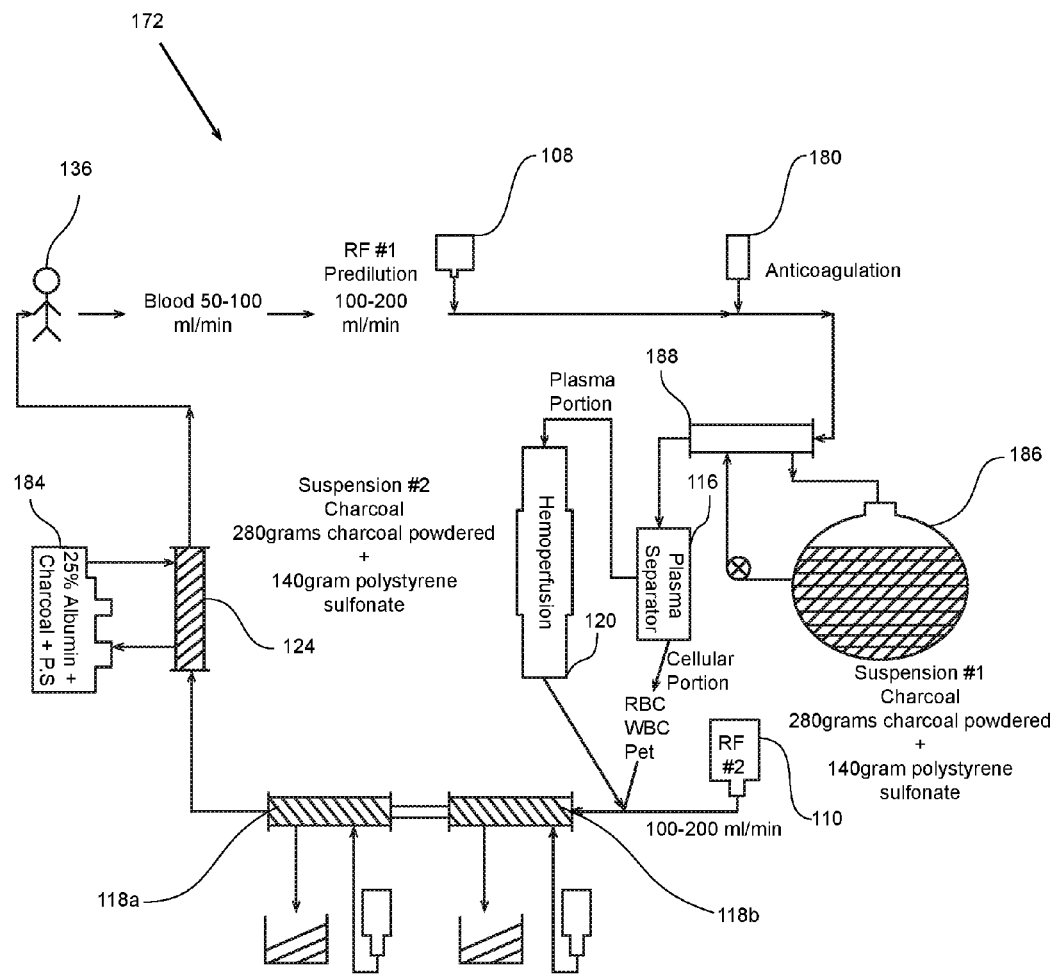
FIG. 14 illustrates a block diagram of a fourteenth embodiment of an exemplary combination kidney and liver dialysis system, in accordance with an embodiment of the present invention.

FIG. 14 illustrates a block diagram of a fourteenth embodiment of an exemplary combination kidney and liver dialysis system 172. The system 172 is configured to perform the functions of separating the blood components, adding large volumes of replacement fluids, passing the plasma portion of the blood through various semi-permeable membranes, and utilizing lipid and albumin dialyzers 160, 122. After the blood leaves the body 136, a dialysate 154 and an anticoagulation fluid 180 are added. The blood then passes through the high flux/high efficiency filter 188. A first solution 186 consisting of 260 grams of powder charcoal and 140 grams polystyrene sulfonate may be added at this point.

A reservoir 184 releases a solution of 25% albumin and charcoal provides filtration for the high molecular weight membrane 124. A plasma separator 116 separates the blood in to a plasma portion and a cellular portion. 100-200 ml of a second replacement fluid 110 is added to the cellular portion. The plasma portion passes through a hemoperfusion membrane 120 before reuniting with the cellular portion. The blood may then pass through the two hemofilters 118a, 118b. Finally, after passing through the high molecular weight membrane 124, a reservoir 184 releases a solution of 25% albumin and charcoal provides filtration for the high molecular weight membrane 124.

Figure 15:
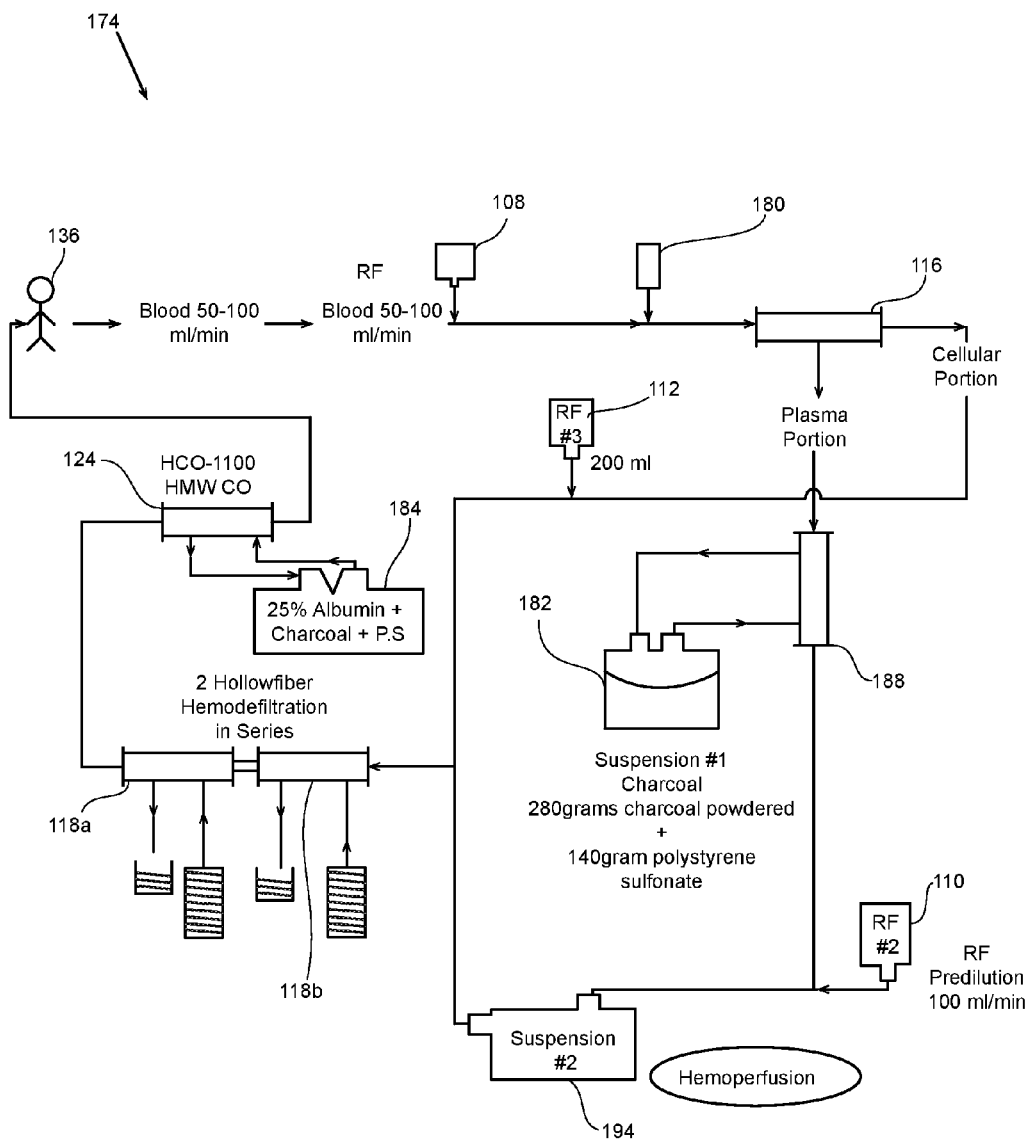
FIG. 15 illustrates a block diagram of a fifteenth embodiment of an exemplary combination kidney and liver dialysis system, in accordance with an embodiment of the present invention.

FIG. 15 illustrates a block diagram of a fifteenth embodiment of an exemplary combination kidney and liver dialysis system 174. The system 174 is configured to perform the functions of separating the blood components, adding large volumes of replacement fluids, passing the plasma portion of the blood through various semi-permeable membranes, and utilizing lipid and albumin dialyzers 160, 122. After the blood leaves the body 136, a dialysate 154 and an anticoagulation fluid 180 are added. A plasma separator 116 separates the blood in to a plasma portion and a cellular portion. The high flux/high efficiency filter 188 exchanges fluids with a second hemoperfusion suspension 194. Next, the blood passes through a first suspension 182 of charcoal. In one embodiment, the first suspension 182 comprises 260 grams of powder charcoal and 140 grams polystyrene sulfonate. Next, a reservoir 184 releases a solution of 25% albumin and charcoal to provide filtration for the high molecular weight membrane 124.

Figure 16:
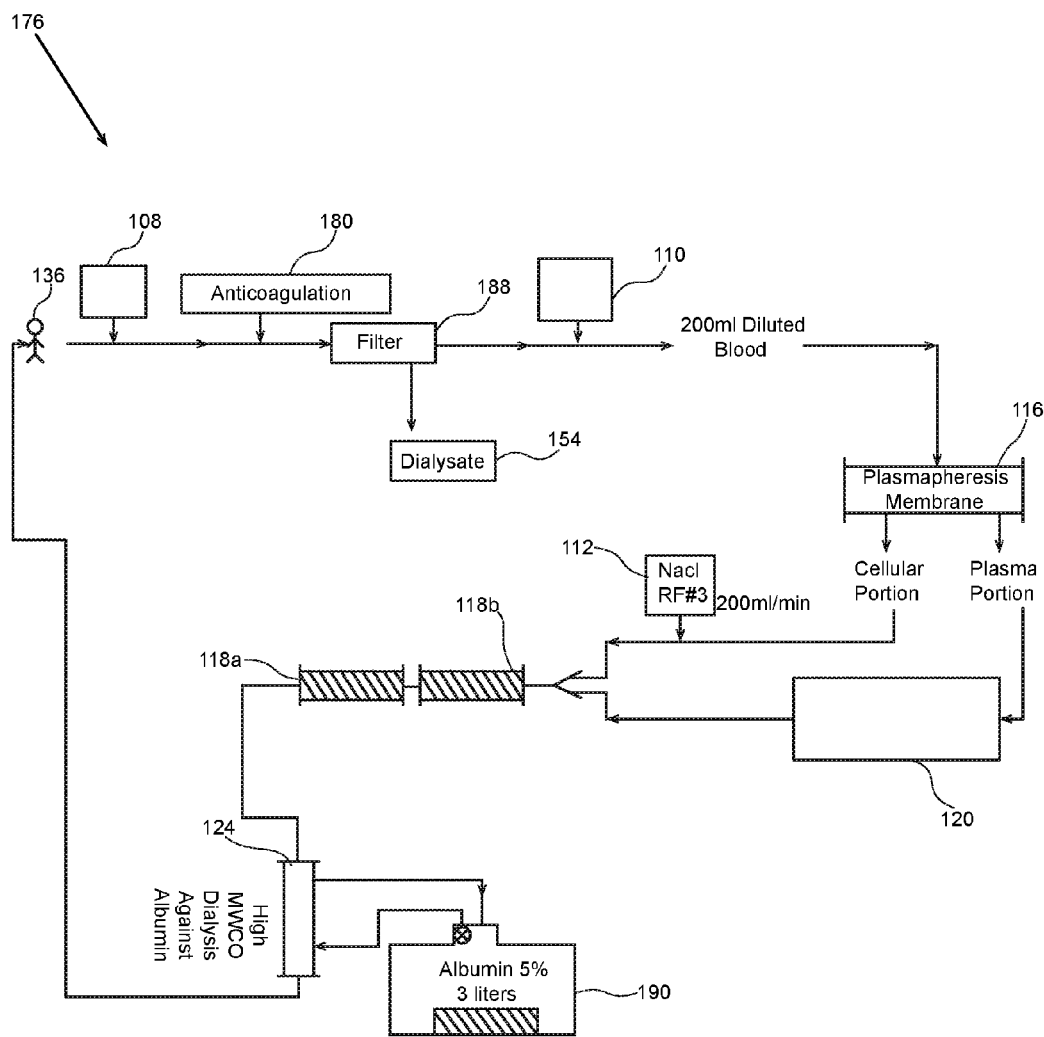
FIG. 16 illustrates a block diagram of a sixteenth embodiment of an exemplary combination kidney and liver dialysis system, in accordance with an embodiment of the present invention.

FIG. 16 illustrates a block diagram of a sixteenth embodiment of an exemplary combination kidney and liver dialysis system 176. The system 176 is configured to perform the functions of separating the blood components, adding large volumes of replacement fluids, passing the plasma portion of the blood through various semi-permeable membranes, and utilizing lipid and albumin dialyzers 160, 122. After the blood leaves the body 136, a dialysate 154 and an anticoagulation fluid 180 are added. A plasma separator 116 separates the blood in to a plasma portion and a cellular portion. A 5% albumin solution 190 is then integrated into the blood at the two hemodiafiltration membranes 118a, 118b. The blood then returns to the body 136 for recirculation.

Figure 17:
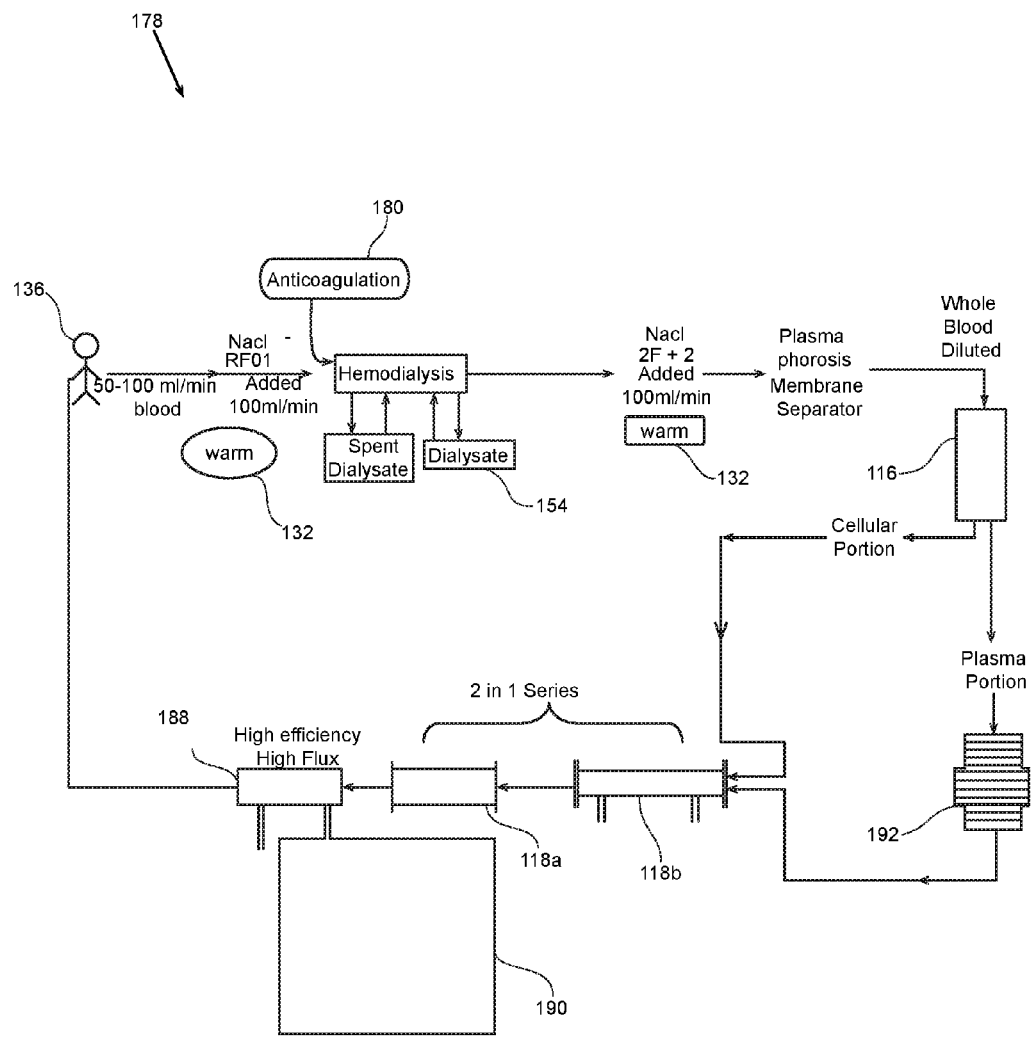
FIG. 17 illustrates a block diagram of a seventeenth embodiment of an exemplary combination kidney and liver dialysis system, in accordance with an embodiment of the present invention.

FIG. 17 illustrates a block diagram of a seventeenth embodiment of an exemplary combination kidney and liver dialysis system 178. The system 178 is configured to perform the functions of separating the blood components, adding large volumes of replacement fluids, passing the plasma portion of the blood through various semi-permeable membranes, and utilizing lipid and albumin dialyzers 160, 122. After the blood leaves the body 136, a dialysate 154 and an anticoagulation fluid 180 are added. A warming device 132 warms the plasma portion of the blood to about 42° Celsius at one or more locations in a circuit/assemblage. A 5% albumin solution 190 is then integrated into the blood. A charcoal and resin filter 192 is also used to help filter the blood. A 5% albumin solution 190 is exchanges fluids with the hemofilters 118a, 118b at the high flux/high efficiency filter 188, before the blood is recirculated back to the body 136.

Figure 18A:
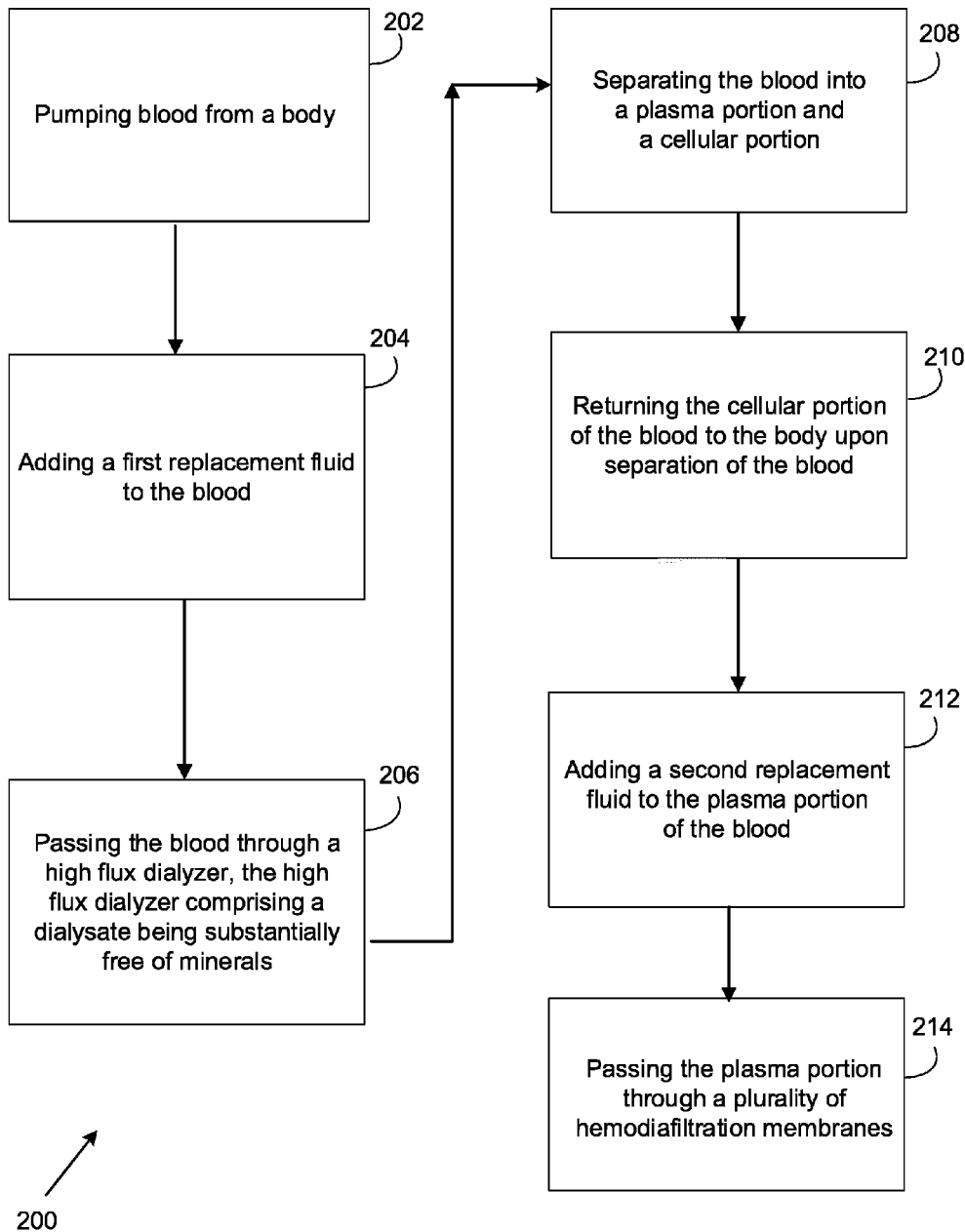
FIGS. 18A and 18B illustrate a flowchart diagram of an exemplary method for treating multiple organ dysfunction syndrome by dialyzing the blood for the kidney and liver, in accordance with an embodiment of the present invention.
Figure 18B:
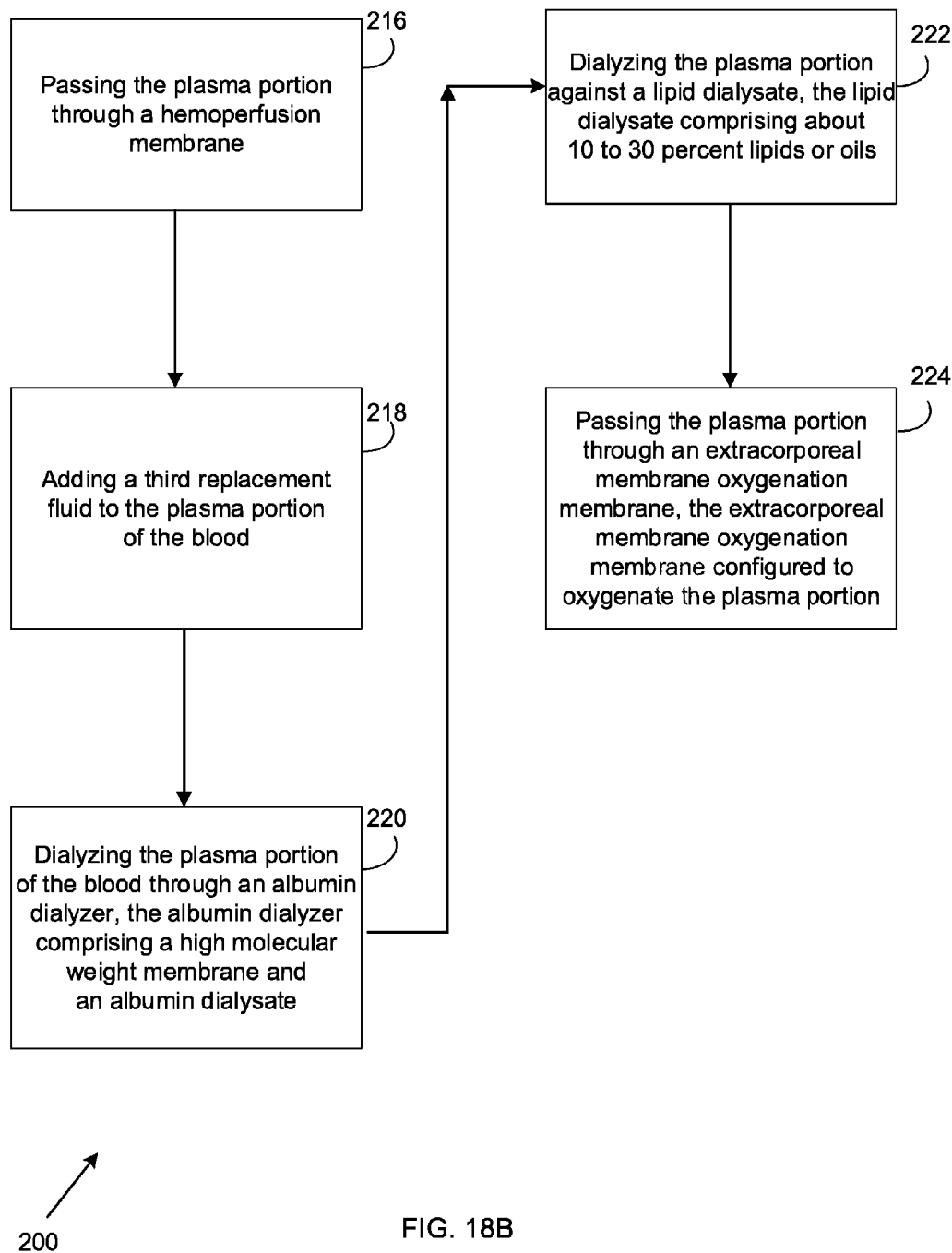

FIGS. 18A and 18B illustrate a flowchart diagram of an exemplary method 200 for treating multiple organ dysfunction syndromes (MODS) by dialyzing the blood for the support of the failing kidney and liver. In one embodiment, the method 200 includes diluting the blood, separating the blood into plasma and cellular portions, returning the cellular portion to the body 136, adding large volumes of replacement fluids 108, 110, 112 to the plasma portion, and passing the plasma portion through strategically placed different types of semi-permeable membranes and absorptive surfaces.

The method comprises an initial Step 202 of pumping the blood from the body 136 of a patient. The blood may be accessed from a first access point 138, and returned to the body 136 through a second access point 140. Multiple pumps working in unison 104 may be used for pumping the blood through the device 102, and to and from the body 136. Another Step 204 may include adding several replacement fluids, the first replacement fluid 108 to the blood. The first replacement fluid 108 is efficacious for diluting the blood. In one embodiment, the first replacement fluid 108 may include different types of physiological fluids such as normal saline with added K and other electrolytes or a mixture consisting of 3 amps of bicarbonate in 1 liter of D5W. In another embodiment, the first replacement fluid 108 is a high concentration ionic solution. The concentration of the first replacement fluid 108 may be altered through a user interface. In some embodiments, the device 102 may include a replacement fluid mixer 106. The replacement fluid mixer 106 dilutes the blood or plasma or its components in 1:1 to 4:1 ratio with the appropriate replacement fluid.

A next Step 206 comprises passing the blood through a high flux dialyzer 114, the high flux dialyzer 114 comprising a standardized dialysate or specially formulated one to address the electrolyte needs of the patient. The high flux dialyzer 114 utilizes a standard dialysate 158 or one consisting of a zero calcium bath to reduce plasma calcium and make the plasma portion of the blood less coagulable. At this point other forms of anticoagulations may be utilized such as regional citrate or heparinization. The method 200 may include a Step 208 of separating the blood into a plasma portion and a cellular portion. In some embodiments, the device 102 includes a membrane plasma separator for plasmapheresis 116. The membrane plasma separator 116 serves to separate the blood leaving the body 136 of the patient into a cellular portion and a plasma portion. It is significant to note than in some embodiments, such as the system 130 of FIG. 2, Step 208 precedes Step 206.

A Step 210 comprises returning the cellular portion of the blood to the body 136 upon separation of the blood. The cellular portion returns to the body 136 through a second access point 140, such as a right arm. In any case, the exit and reentry of the blood occurs at separate locations of the body 136 to minimize recirculation of the blood. The method 200 may further include a Step 212 of adding a second replacement fluid 110 to the plasma portion of the blood. The second replacement fluid 110 is efficacious for diluting the blood. In one embodiment, the second replacement fluid 110 may include a high concentration ionic solution. The concentration of the second replacement fluid 110 may be altered through the user interface.

An additional Step 214 includes passing the plasma portion through at least one hemodiafiltration membrane 118a, 118b. The hemodiafiltration of the pre-diluted plasma portion occurs via a first hemofilter 118a and a second hemofilter 118b if desired which is optional. The two hemofilters 118a, 118b are configured to be densely packed and have a short length and high intra-fiber diameters ratio. In one possible embodiment, the hemofilters have an internal diameter as low as one hundred microns—the lower limit of hollow fiber technology, since there is no cellular component in this portion of the dialysis. The two hemofilters 118a, 118b may be connected in series while performing the hemodiafiltration and hemofiltration functions.

A further Step 216 comprises passing the plasma portion through a hemoperfusion membrane 120. The hemoperfusion may occur via a container containing suspension of activated charcoal and polystyrene sulfonate and other resins. The method 200 may further include a Step 218 of adding a third replacement fluid 112 to the plasma portion of the blood. The third replacement fluid 112 is efficacious for diluting the blood. In one embodiment, the third replacement fluid 112 may include a high concentration ionic solution. The concentration of the third replacement fluid 112 may be altered through the user interface.

The method 200 may further include a Step 220 of dialyzing the plasma portion of the blood through an albumin dialyzer 122, the albumin dialyzer 122 comprising a high molecular weight cut off membrane 124 and an albumin dialysate 154, the albumin dialysate 154 comprising at least one of the following: either albumin solution or combination with activated charcoal, covered with polystyrene sulfonate, and/or resin. The albumin dialyzer 122 utilizes a high molecular weight cut off membrane 124, whereby the plasma portion flows through the high molecular weight cut off membrane 124 and the albumin dialysate 154 flows on the opposite side of the high molecular weight cut off membrane 124.

In some embodiments, the method 200 may include a Step 222 of dialyzing the plasma portion against a lipid dialysate 156, the lipid dialysate 156 comprising about 10% to 30% lipids or oils, such as intralipid. In one embodiment, the plasma portion passes through a lipid dialyzer 160 against the lipid dialysate 156, after passing through the high molecular weight cut off membrane 124 of the albumin dialyzer 122.

An additional Step 224 may include passing the cellular portion and/or the plasma portion of the blood through an extracorporeal membrane oxygenation membrane 126, the extracorporeal membrane oxygenation membrane 126 configured to oxygenate the cellular portion and/or the plasma portion of the blood. The extracorporeal membrane oxygenation membrane 126 is configured to oxygenate the plasma portion of the blood before reentering the body 136. The blood is pumped back into the body 136 at a second access point 140, such as a right arm. It is significant to note that the use of two access points 138, 140 reduces excessive circulation of blood. Additionally, after the blood is oxygenated, the plasma portion is returned to the body 136 of the patient through a second access point 140, such as a right arm. The first and second access points 138, 140 are generally opposite of each other to minimize circulation of the blood.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

What I claim is:

1. A system for treating multiple organ dysfunction syndrome through a complex multicomponent hemodialysis device, the system comprising:
    at least one pump, the at least one pump configured to enable pumping of blood;
    at least one replacement fluid mixer, the at least one replacement fluid mixer configured to enable adding at least one replacement fluid to the blood;
    a membrane plasma separator, the membrane plasma separator configured to enable separation of the blood into a cellular portion and a plasma portion;
    a high flux dialyzer, the high flux dialyzer comprising different dialysates having a low concentration of minerals;
    a plurality of hemodiafiltration membranes;
    a hemoperfusion membrane, the hemoperfusion membrane defined by high molecular weight cut off;
    an albumin dialyzer, the albumin dialyzer comprising a high molecular weight cut off membrane and an albumin dialysate, the albumin dialysate comprising at least one of the following: a 5%-25% albumin solution, an activated charcoal, a polystyrene sulfonate, and resin;
    a lipid dialysate, the lipid dialysate comprising about 10 to 30 percent lipids or oils; and
    an extracorporeal membrane oxygenation membrane, the extracorporeal membrane oxygenation membrane configured to enable at least partial oxygenation of the cellular portion of the blood.

2. The system of claim 1, wherein the at least one replacement fluid comprises a first replacement fluid, a second replacement fluid, and a third replacement fluid.

3. The system of claim 2, wherein the first replacement fluid is a mixture consisting of 3 amps of bicarbonate in 1 liter of D5W.

4. The system of claim 1, wherein the plurality of hemodiafiltration membranes comprising a first hemofilter and a second hemofilter arranged in series or only one hemodiafiltration.

5. The system of claim 1, wherein the membrane plasma separator and a plasmapheresis membrane are configured to separate the blood into a ratio of plasma portion to cellular portion by volume.

6. The system of claim 5, wherein the ratio comprises at least one of the following: 1:1, 2:1, and 3:1.

7. The system of claim 1, wherein the dialysate of the high flux dialyzer comprises a standard dialysate or a calcium bath concentration.

8. The system of claim 7, wherein the calcium bath concentration comprises a zero calcium bath-optional.

9. The system of claim 1, wherein the plurality of hemodiafiltration membranes comprise a first hemofilter and a second hemofilter, the first hemofilter and the second hemofilter disposed in a circuit and connected in series or in parallel.

10. The system of claim 1, wherein the hemoperfusion membrane comprises a suspension that includes at least one member selected from the group consisting of: an activated charcoal, a polystyrene sulfonate, and a resin operable as a dialysate.

11. The system of claim 1, wherein the lipid dialysate comprises different biocompatible lipid emulsions for human intravenous use commonly used in partial parenteral nutrition and/or total parenteral nutrition approved by FDA for use intravenously in human subjects such as intralipid.

12. The system of claim 1, further including a warming device, the warming device configured to warm the plasma portion to about 42 degrees Celsius at one or more locations in a circuit/assemblage.

13. The system of claim 12, wherein the warming device is operable in different portions of the circuit/assemblage, the warming device configured to increase diffusion of a substance.

14. The system of claim 13, wherein the warming device is configured to warm the plasma portion at different location in the circuit/assemblage.

15. The system of claim 14, further including a cooling device, the cooling device configured to cool the plasma portion up to 35 degrees Celsius at various locations in the circuit/assemblage.

16. The system of claim 15, wherein the cooling device is configured to cool the plasma portion after passing through the albumin dialyzer.

17. A method for treating multiple organ dysfunction syndrome through dialysis of blood, the method comprising:
    pumping blood from a body;
    adding a first replacement fluid to the blood;
    passing the blood through a high flux dialyzer, the high flux dialyzer comprising a standard dialysate or a low calcium bath;
    separating the blood into a plasma portion and a cellular portion;
    returning the cellular portion of the blood to the body upon separation of the blood;
    adding a second replacement fluid to the plasma portion of the blood;
    passing the plasma portion through a plurality of hemodiafiltration membranes;
    passing the plasma portion through a hemoperfusion membrane;
    adding a third replacement fluid to the plasma portion of the blood;

dialyzing the plasma portion of the blood through an albumin dialyzer, the albumin dialyzer comprising a high molecular weight cut off membrane and an albumin dialysate, the albumin dialysate comprising at least one of the following: albumin, activated charcoal, a polystyrene sulfonate, and resin;

dialyzing the plasma portion against a lipid dialysate, the lipid dialysate comprising about 10 to 30 percent lipids or oils by weight or volume; and passing the cellular portion through an extracorporeal membrane oxygenation membrane, the extracorporeal membrane oxygenation membrane configured to oxygenate the cellular portion.

18. The method of claim 17, further including the step of warming the plasma portion after passing through the albumin dialyzer and hemodiafiltration portion.

19. The method of claim 17, further including the step of passing the blood through a high flux dialyzer a second time for discarding ultrafiltration.

20. A system for treating multiple organ dysfunction syndrome through a multi-component hemodialysis device, the system comprising:

at least one replacement fluid mixer, the at least one replacement fluid mixer configured to enable adding several replacement fluids to the blood and its portions in prespecified positions;

a membrane plasma separator, the membrane plasma separator having a plasmapheresis membrane, the membrane plasma separator configured to enable separation of the blood into a cellular portion and a plasma portion;

a high flux dialyzer, the high flux dialyzer comprising a standard dialysates and a dialysate having a low concentration of calcium;

at least one hemofilter, the at least one hemofilter comprising hollow fibers defined by a small diameter;

a hemodialysis filter, the hemodialysis filter disposed in series with the at least one hemofilter;

a hemoperfusion membrane, the hemoperfusion membrane comprising activated microporous charcoal and a resin; and an albumin dialyzer, the albumin dialyzer comprising a high molecular weight cut off membrane and an albumin dialysate, the albumin dialysate comprising at least one of the following: a 5%-25% albumin solution alone or in solution with activated charcoal, polystyrene sulfonate, and second resin.

21. The system of claim 20, further including a lipid dialyzer comprising a lipid dialysate, the lipid dialysate comprising about 10 to 30 percent lipids or oils by weight or volume.

22. The system of claim 21, wherein the lipids or oils comprise inert and biocompatible lipids or oils.

23. The system of claim 22, further including an extracorporeal membrane oxygenation membrane, the extracorporeal membrane oxygenation membrane configured to enable at least partial oxygenation of the cellular portion of the blood before it is returned back to the patient.

24. The system of claim 23, wherein the system is based on a microfluidic technology.

25. The system of claim 24, wherein the microfluidic technology is operable with at least one of the following: the replacement fluid mixer, the membrane plasma separator, the high flux dialyzer, the at least one hemofilter, the hemodialysis filter, the hemoperfusion membrane, the albumin dialyzer, the lipid dialyzer, and the extracorporeal membrane oxygenation membrane.

* * * * *